US011096929B2

(12) United States Patent
During

(10) Patent No.: US 11,096,929 B2
(45) Date of Patent: Aug. 24, 2021

(54) METHODS OF TREATING DEVELOPMENTAL DISORDERS WITH GABOXADOL

(71) Applicant: Ovid Therapeutics Inc., New York, NY (US)

(72) Inventor: Matthew During, Weston, CT (US)

(73) Assignee: OVID THERAPEUTICS INC., New York, NY (US)

( * ) Notice: Subject to any disclaimer, the term of this patent is extended or adjusted under 35 U.S.C. 154(b) by 0 days.

(21) Appl. No.: 16/221,794

(22) Filed: Dec. 17, 2018

(65) Prior Publication Data

US 2019/0117632 A1    Apr. 25, 2019

Related U.S. Application Data

(63) Continuation of application No. 16/053,343, filed on Aug. 2, 2018, now abandoned, which is a continuation of application No. 15/840,521, filed on Dec. 13, 2017, now abandoned, which is a continuation of application No. 15/209,862, filed on Jul. 14, 2016, now abandoned, and a continuation of application No. 15/616,460, filed on Jun. 7, 2017, now abandoned.

(60) Provisional application No. 62/346,763, filed on Jun. 7, 2016, provisional application No. 62/332,567, filed on May 6, 2016, provisional application No. 62/207,595, filed on Aug. 20, 2015, provisional application No. 62/193,717, filed on Jul. 17, 2015.

(51) Int. Cl.
*A61K 31/437* (2006.01)
*A61P 25/14* (2006.01)
*A61P 25/00* (2006.01)

(52) U.S. Cl.
CPC ............ *A61K 31/437* (2013.01); *A61P 25/00* (2018.01); *A61P 25/14* (2018.01)

(58) Field of Classification Search
CPC ............................. A61K 31/437; A61P 25/00
See application file for complete search history.

(56) References Cited

U.S. PATENT DOCUMENTS

| 2,830,083 | A | 4/1958 | Gilbert et al. |
| 4,084,000 | A | 4/1978 | Fuxe |
| 4,129,652 | A | 12/1978 | Fuxe |
| 4,138,484 | A | 2/1979 | Fuxe |
| 4,278,676 | A | 7/1981 | Krogsgaard-Larsenpovl |
| 4,353,910 | A | 10/1982 | Perregaard |
| 4,362,731 | A | 12/1982 | Hill |
| 4,778,794 | A | 10/1988 | Naruse et al. |
| 5,948,433 | A | 9/1999 | Burton et al. |
| 5,985,311 | A | 11/1999 | Cordes et al. |
| 6,461,644 | B1 | 10/2002 | Jackson et al. |
| 6,676,961 | B1 | 1/2004 | Lichter |
| 9,339,495 | B2 | 5/2016 | During |
| 9,351,968 | B1 | 5/2016 | During |
| 9,399,034 | B1 | 7/2016 | During et al. |
| 9,446,028 | B2 | 9/2016 | During |
| 9,682,069 | B2 | 6/2017 | During |
| 9,717,716 | B2 | 8/2017 | During et al. |
| 10,071,083 | B2 | 9/2018 | During |
| 2003/0077297 | A1 | 4/2003 | Chen et al. |
| 2005/0171142 | A1* | 8/2005 | Cooper ............... A61P 25/16 514/302 |
| 2005/0234093 | A1* | 10/2005 | Sanchez ............ A61P 25/00 514/302 |
| 2007/0112017 | A1 | 5/2007 | Barlow et al. |
| 2007/0259912 | A1 | 11/2007 | Cooper |
| 2008/0269278 | A1 | 10/2008 | Lundahl et al. |
| 2009/0143335 | A1* | 6/2009 | Larsen ............... A61K 31/437 514/81 |
| 2010/0029770 | A1 | 2/2010 | Roberts et al. |
| 2011/0046090 | A1 | 2/2011 | Barlow et al. |
| 2013/0251671 | A1 | 9/2013 | Kaufman et al. |
| 2013/0309306 | A1 | 11/2013 | Rogawski et al. |
| 2015/0313913 | A1 | 11/2015 | Catterall et al. |
| 2015/0352085 | A1 | 12/2015 | During |
| 2016/0038469 | A1 | 2/2016 | During |

(Continued)

FOREIGN PATENT DOCUMENTS

| CN | 102147667 A | 8/2011 |
| EP | 0000338 A2 | 1/1979 |

(Continued)

OTHER PUBLICATIONS

Dech et al., J. Am. Acad. Child Adolesc Psychiatry vol. 30 pp. 298-302. Published 1991 (Year: 1991).*
Dech et al., J. Am. Acad Child Adolesc Psychiatry vol. 30 pp. 298-302. Published 2001 (Year: 2001).*
Reagan-Shaw et al., FASEBJ vol. 22 pp. 659-661. Published 2007. (Year: 2007).*
Butler et al., British Journal of Anaesthesia vol. 103 Supplement 15 published 2009 (Year: 2009).*
Dech (J. Am. Acad. Child Adolesc. Psychiatry vol. 30 pp. 298-302 (1991) (Year: 1991).*

(Continued)

*Primary Examiner* — Theodore R. Howell
*Assistant Examiner* — George W Kosturko
(74) *Attorney, Agent, or Firm* — Carter, DeLuca & Farrell LLP

(57) ABSTRACT

Methods of treating developmental disorders such as Angelman syndrome, Fragile X syndrome, Fragile X-associated tremor/ataxia syndrome (FXTAS), Autistic Spectrum Disorder, Autism, Asperger's syndrome, pervasive developmental disorder, Childhood Disintegrative Disorder, Rett syndrome, Lanau-Kleffner Syndrome, Prader-Willi Syndrome, Tardive Dyskinesia, and/or Williams Syndrome with gaboxadol or a pharmaceutically acceptable salt thereof are provided. The methods provide therapeutic compositions that may be used to improve one or more symptoms of the developmental disorder.

13 Claims, 2 Drawing Sheets

(56) References Cited

U.S. PATENT DOCUMENTS

| | | |
|---|---|---|
| 2016/0228418 A1 | 8/2016 | During |
| 2017/0014392 A1 | 1/2017 | During |
| 2017/0014393 A1 | 1/2017 | During |
| 2017/0065572 A1 | 3/2017 | During |
| 2017/0348232 A1 | 12/2017 | During |
| 2018/0042903 A1 | 2/2018 | During |
| 2018/0098974 A1 | 4/2018 | During |
| 2018/0235942 A1 | 8/2018 | During et al. |
| 2018/0338960 A1 | 11/2018 | During |

FOREIGN PATENT DOCUMENTS

| | | | |
|---|---|---|---|
| EP | 0840601 B1 | 10/2001 | |
| EP | 3372229 A1 | 9/2018 | |
| WO | 9702813 A1 | 1/1997 | |
| WO | WO-0243731 A2 * | 6/2002 | ........... A61K 31/255 |
| WO | 2005094820 A1 | 10/2005 | |
| WO | 2006013397 A1 | 2/2006 | |
| WO | 2008095253 A1 | 8/2008 | |
| WO | 2013056159 A1 | 4/2013 | |
| WO | 2014085668 A1 | 6/2014 | |
| WO | 2014123909 A1 | 8/2014 | |
| WO | 2015189744 A1 | 12/2015 | |

OTHER PUBLICATIONS

Chen et al., "A Sutdy of Central Nervous System Stimulants," J. Pharmacology Experimental Therapeutics, vol. 123, Mar. 17, 1958; pp. 212-215.

Cheng et al., "Inducing Anesthesia with a GABA Analog, THIP,", Anesthesiology, vol. 63, No. 2, Aug. 1985; pp. 147-151.

Ebert et al., "Treating Insomnia: Current and Investigational Pharmacological Approaches," Pharmacology & Therapeutics, vol. 112, 2006; pp. 612-629.

McCaffery et al. "Policy and Procedure on Conscious Sedation/Analgesia for Adults," Pain: Clinical Manual (1996); 10 pages.

Sessler et al., Semin. Respir. Crit. Care Med. (2013), vol. 34(2), pp. 169-178.

Walsh et al. "The Selective Extrasynaptic GABAA Agonist, Gaboxadol, Improves Traditional Hypnotic Efficacy Measures and Enhances Slow Wave Activity in a Model of Transient Insomnia," Sleep, vol. 30, No. 5, 2007; pp. 593-602.

Stephanie Saul, "Merck Cancels Work on a New Insomnia Medication," The New York Times, Business Day, Mar. 29, 2007; http://www.nytimes.com/2007/03/29/business/29sleep.html?.sub.-r=0; 3 pages.

Hughes et al., "Sedation in the Intensive Care Setting," Clinical Pharmacology: Advances and Applications, (Dovepress) vol. 4, 2012; pp. 53-63.

Ransdell Pierson, "Update 2-Merck, Lundbeck scrap insomnia drug after trials," Rueters, (Dow Jones); 2015; 2 pages.

Egawa et al., Decreased Tonic Inhibition in Cerebellar Granule Cells Causes Motor Dysfunction in a Mouse MOdel of Angelman Syndrome, Neurodegenerative Disease, Science Translational Medicine, vol. 4, Issue 165 (163ra157), Dec. 5, 2012. pp. 1-10.

James K. Walsh, Ph.D., "Enhancement of Slow Wave Sleep: Implications for Insomnia," Journal of Clinical Sleep Medicine, Supplement to vol. 5, No. 2, (2009); pp. 827-832.

Wang et al., "Neurobiology of Disease—The Melatonin MT1 Receptor Axis Modulates Mutant Huntingin-Mediated Toxicity," The Journal of Neuroscience, vol. 31, No. 41, Oct. 12, 2011; pp. 14496-14507.

Williams et al., "Conference Report—Angelman Syndrome 2005: Updated Consensus for Diagnostic Criteria," American Journal of Medical Genetics, vol. 140A 2006; pp. 413-418.

Braat et al., "Fragile X Syndrome Neurobiology Translates Into Rational Therapy," Drug Discovery Today, vol. 00, No. 30, Feb. 2014; pp. 1-10.

International Search Report and Written Opinion of the International Searching Authority, dated Aug. 26, 2015, corresponding to International Application No. PCT/US15/34018; 12 total pages.

Olmos-Serrano et al, "Defective GABAergic Neurotransmission and Pharmacological Rescue of Neuronal Hyperexcitability in the Amygdala in a Mouse Model of Fragile X Syndrome," The Journal of Neuroscience, vol. 30, No. 29, Jul. 21, 2010; pp. 9929-9938 (25 pages).

Walter, Alexander, "Sleep: Gaboxadol Enhances Slow Wave Sleep," Perelman, School of Medicine, Jun. 22, 2006; 3 pages.

Brown et al., "Microarray Identification of FMRP—Associated Brain mRNAs and Altered mRNA Translational Profiles in Fragile X Syndrome," Cell, vol. 107, Nov. 16, 2001; pp. 477-487.

Brown et al., "Pharmacological Characterization of a Novel Cell Line Expressing Human ?4?3? GABAA Receptors," British Journal of Pharmacology, vol. 136, No. 7, 2002; pp. 965-974.

Sarah DeWeerdt, "Fragile X Mice Show Brain-Wave Abnormalities During Sleep," SFARI, Simons Foundation, Autism Research Initiative, Jan. 25, 2013; 2 pages.

Deacon et al., "Effect of Short-Term Treatment with Gaboxadol on Sleep Maintenance and Initiation in Patients with Primary Insomnia," Sleep, vol. 30, No. 3, 2007; pp. 281-287.

Faulhaber et al., "The GABAA Agonist THIP Produces Slow Wave Sleep and Reduces Spindling Activity in NREM Sleep in Humans," Psychopharmacology, vol. 130, 1997; pp. 285-291.

Fox et al., "Transdermal Drug Delivery Enhancement by Compounds of Natural Origin," Molecules, vol. 16, 2011; pp. 10507-10540.

Gaboxadol, from Wikipedia, the free encylopedia,http://en.wikipedia.org/wiki/Gaboxadol, 2014; 2 pages.

Gaboxadol, Investigational Agent—Drug Development Technology, http//www.drugdevelopment-technology.com/projects/gaboxadol-2014; 3 pages.

Gaboxadol, Bluelight, http://www.bluelight.org/vb/threads/370965-Gaboxadol—(2014); 1 page.

Glykys et al., "The Main Source of Ambient Gaba Responsible for Tonic Inhibition in the Mouse Hippocampus," J Physiol, vol. 582, No. 3, 2007; pp. 1163-1178.

Hajak et al., "A 2-week Efficacy and Safety Study of Gaboxadol and Zolpidem Using Electronic Diaries in Primary Insomnia Outpatients," Sleep Medicine, vol. 10, 2009; pp. 705-712.

Iber et al., "The AASM Manual for the Scoring of Sleep and Associated Events," American Academy of Sleep Medicine (2007); pp. 3-59 (57 pages).

Jennum et al., "Sleep Disorders in Neurodegenerative Disorders and Stroke," European Handbook of Neurological Management, vol. 1, 2nd Edition, Chapter 39, Section 6—Sleep Disorders, (Ed. Gilhus et al.) Blackwell Publishing Ltd. 2011; pp. 529-543.

Jonas et al., "Neural Inhibition,", Scholarpedia—http://www.scholarpedia.org/article/Neural.sub.-inhibition-(2014); 10 pages.

Lancel et al., "The GABAA Agonist THIP (Gaboxadol) Increases Non-REM Sleep and Enhances Delta Activity in the Rat," Sleep and Rhythms, NeuroReport, Rapid Science Publishers, vol. 7, No. 13; Sep. 1996; pp. 2241-2245.

Marike Lancel, "The GABAA Agonist THIP Increases Non-REM Sleep and Enhances Non-REM Sleep-Specific Delta Activity in the Rat During the Dark Period," Sleep, vol. 20, No. 12, American Sleep Disorders Association and Sleep Research Society (1997); pp. 1099-1104.

Marike Lancel, "Role of GABAA Receptors in the Regulation of Sleep: Initial Sleep Responses to Peripherally Administered Modulators and Agonists," Sleep, vol. 22, No. 1, (1999); pp. 33-42.

Lancel et al., "Effect of the GABAA Agonist Gaboxadol on Nocturnal Sleep and Hormone Secretion in Healthy Elderly Subjects," Am J. Physiol Endoctrinol Metab, vol. 281; (2001), pp. E130-E137.

Larsen et al., -Research Paper—"Intestinal Gaboxadol Absorption via Pati (SLC36A1): Modified Absorption in vivo Following Co-administration of L-tryptophan," British Journal of Pharmacology (BJP), vol. 157, (2009); pp. 1380-1389.

Lundahl et al., "Short-term Treatment with Gaboxadol Improves Sleep Maintenance and Enhances Slow Wave Sleep in Adult Patients with Primary Insomnia," Psychopharmacology, vol. 195, (2007); pp. 139-146.

(56) References Cited

OTHER PUBLICATIONS

Mathias et al., "The GABAA Agonist Gaboxadol Improves the Quality of Post-Nap Sleep," Psychopharmacology, vol. 157 (2001); pp. 299-304.
Mathias et al., "Effect of Repeated Gaboxadol Administration on Night Sleep and Next-Day Performance in Healthy Elderly Subjects," Neuropsychopharmacology, vol. 30, (2005) pp. 833-841.
Natural Patterns of Sleep—Healthy Sleep—http://healthysleep.med.harvard.edu/healthy/science/what/sleep-pat-terns-rem-nrem (2007); 3 pages.
Olmos-Serrano et al, "The GABAA Receptor Agonist Thip Ameliorates Specific Behavioral Deficits in the Mouse Model of Fragile X Syndorme," Developmental Neuroscience, vol. 33, Fragile X Syndrome/Review, (2011), pp. 395-403.
Pathan et al, "Chemical Penetration Enhancers for Transdermal Drug Delivery Systems," Tropical Journal of Pharmaceutical Research, vol. 8, No. 2 (2009); pp. 173-179.
Tropea et al., "Partial Reversal of Rett Syndrome-like Symptoms in MeCP2 Mutant Mice," PNAS, vol. 106, No. 6, Feb. 10, 2009; pp. 2029-2034.
Vardya et al., "Positive Modulation of ?-Subunit Containing GABAA Receptors in Mouse neurons" Neuropharmacology, vol. 63; 2012; pp. 469-479.
International Search Report and Written Opinion of the International Searching Authority, dated Sep. 27, 2016, corresponding to International Application No. PCT/US16/42238; 8 total pages.
Webb, et al., "The frequency of the fragile X chromosome among schoolchildren in Coventry", Journal of Medical Genetics, 1986, vol. 23; pp. 396-399.
Egawa et al., "Pathophysiological power of improper tonic GABA(A) conductances in mature and immature models." Frontiers in Neural Circuits, Oct. 2013, vol. 7, Article 170; pp. 1-15.
Youings, et al., FRAXA and FRAXE: the results of a five year survey. J. Med. Genet. 2000, vol. 37: pp. 415-421.
Crawford, et al., "FMR1 and the Fragile X Syndrome: Human Genome Epidemiology Review," Genet. Med. 2001, vol. 3, No. 5 (Author Manuscript); pp. 359-371.
Crawford, et al., "Prevalence of the Fragile X Syndrome in African-Americans," American Journal of Medical Genetic (Jul. 1, 2002), vol. 110, Issue 3: pp. 226-233.
Miyashiro et al., "RNA Cargoes Associating with FMRP Reveal Deficits in Cellular Functioning in Fmr1 Null Mice" Neuron, Feb. 6, 2003, vol. 37; pp. 417-431.
Dictenberg et al., "A Direct Role for Fmrp in Activity-Dependent Dendritic mRNA Transport Links Filopodial-Spine Morphogenesis to Fragile X Syndrome," Dev Cell (Jun. 2008), vol. 14, No. 6 (Author Manuscript); pp. 926-939.
Braat et al., "The GABAA receptor is an FMRP target with therapeutic potential in fragile X syndrome," Cell Cycle (Sep. 15, 2015) vol. 14, No. 18; pp. 2985-2995.
Braat et al., "Insights into GABAAergic system deficits in fragile X syndrome lead to clinical trials," Neuropharmacology (Jan. 2015), vol. 88; pp. 48-54.
Curia et al., "Downregulation of Tonic GABAergic Inhibition in a Mouse Model of Fragile X Syndrome," Cerebral Cortex (Jul. 2009), vol. 19; pp. 1515-1520.
El Idrissi et al., "Decreased GABA(A) receptor expression in the seizure-prone fragile X mouse," Neurosci Lett (2005) vol. 377, No. 3; pp. 141-146.
Gantois et al., "Expression profiling suggests underexpression of the GABA(A) receptor subunit delta in the fragile X knockout mouse model, " Neurobiol Dis (2006), vol. 21, No. 2; pp. 346-357.
Turner et al., "Preventive Screening for the Fragile X Syndrome," The New England Journal of Medicine (1986), vol. 315, No. 10; pp. 607-609.
Turner et al., "Prevalence of fragile X syndrome," Am. J. Med. Genet. (1996), vol. 64; pp. 196-197.
Martin et al., "Deficient Tonic GABAergic conductance and synaptic balance in the fragile X sydrome amygdala,", J. Neurophysiol (May 21, 2014), vol. 112, pp. 890-902.

Bradford et al., "Incidence of Fragile X Syndrome by Newborn Screening for Methylated FMR1 DNA," The American Journal of Human Genetics (Oct. 9, 2009), vol. 85; pp. 503-514.
Lozano et al., "Modulation of the GABAergic pathway fro the treatment of fragile X syndrome", Neuropsychiatric Disease and Treatment (2014), vol. 10 (Dovepress); pp. 1769-1779.
Kazdoba et al, "Modeling fragile X syndrome in the Fmr1 knockout mouse," Intractable & Rare Diseases Research (2014), vol., 3, No. 4; pp. 118-133.
Paluszkiewicz et al., "Fragile X Syndrome: The GABAergic System and Circuit Dysfunction," Developmental Neuroscience (2011); vol. 33; pp. 349-364.
Rio et al., The contribution of inhibitory interneurons to cirecuit dysfunction in Fragile X Syndrome, Froneiers in Cellular Neuroscience (Aug. 25, 2014), vol. 8, Article 245; pp. 1-7.
PCT Notice concerning Transmittal of International Preliminary Report on Patentability (Chapter I of the Patent Cooperation Treaty), International Preliminary Report on Patentability and Written Opinion of the International Searching Authority, dated Feb. 1, 2018, corresponding to International Application No. PCT/US2016/042238; 8 total pages.
Egawa et al., "Decreased Tonic Inhibition in Cerebellar Granule Cells Causes Motor Dysfunction in a Mouse Model of Angelman Syndrome", Neurodegenerative Disease, Research Article, Science Translational Medicine, vol. 4, Issue 163 (163ra157); Dec. 5, 2012; 32 pages.
European Search Report dated Feb. 13, 2019, corresponding to European Application No. 16828266.3; 11 pages.
Thacker et al., "Brain γ-Aminobutyric Acid Abnormality in Tardive Dyskinesia," Arch Gen Psychiatry, vol. 44, Jun. 1987; pp. 522-529.
Peixoto et al., "Effecxts of gabaergic drugs on reserpine-induced oral dyskinesia," Behavioural Brain Research, vol. 160, (2005); pp. 51-59.
Reagan-Shaw et al., "Dose translation from animal to human studies revisited", FASEB J, vol. 22, No. 3, Oct. 17, 2007; pp. 659-661.
International Search Report and Written Opinion of the International Searching Authority, dated Aug. 14, 2015, corresponding to International Application No. PCT/US2015/029155; 19 total pages.
Oakley et al., "Synergistic GABA-Enhancing Therapy against Seizures in a Mouse Model of Dravet Syndrome," The Journal of Pharmacology and Experimental Therapeutics, vol. 345, May 2013; pp. 215-224.
Hagerman et al., "Treatment of fragile X-associated tremor ataxia syndrome (FXTAS) and related neurological problems", Clinical Intervention in Aging, 2008, vol. 3, No. 2; pp. 251-262.
Nagar et al., "Orally disintegrating tablest: formulation, preparation techniques and evaluation", Journal of Applied Phramaceutical Science, vol. 01, No. 04, 2011; pp. 35-45.
Hagerman et al., "Fragile X-associated tremor/ataxia syndrome", Annals of the New York Academy of Sciences, Issue: The Year in Nurology and Psychiatry, (ISSN 0077-8923), 2015; pp. 1-13.
Gupta Nitan Bharti et al., "Pulsatile Drug Delivery as Modified Release Dosage Form: A Review", Journal of Drug Delivery & Therapeutics, vol. 2, No. 6, 2012; pp. 102-110.
Reddy et al., "Review on: Pulsatile Drug Delivery Systems", Journal of Pharmacetucial Sciences and Research, (ISSN: 0975-1459), vol. 1, No. 4, 2009; pp. 109-115.
The United States Pharmacopeia (USP) disintegration test method set forth at section 701 Disintegration, Revision Bulletin Official Aug. 1, 2008; pp. 1-3.
Bharawaj et al., "Orally Disintegrating Tablets: A Review", Drug Invention Today, vol. 2, No. 1, (ISSN: 0975-7619), 2010; pp. 81-88.
Boyle et al., "Tolerability, pharmacokinetics and night-time effects on postural sway and critical flicker fusion of gaboxadol and zolpidem in elderly subjects," British Journal of Clinical Pharmacology, 2008, vol. 67, No. 2; pp. 180-190.
Guidance for Industry, Orally Disintegrating Tablets, United States Department of Health and Human Services, Food and Drug Administraction, Center for Drug Evaluation and Research (CDER), Dec. 2008, Chemistry, pp. 1-8.
Yapar et alo., "Orally Disintegrating Tablets: An Overview," Journal of Applied Pharmaceutical Science, Feb. 2014, vol. 4, No. 02, pp. 118-125.

(56) References Cited

OTHER PUBLICATIONS

Fu et al., "Drug Release Kinetics and Transport Mechanisms of Non-degradable and Degradable Polymeric Delivery Systems," NIH Public Access, Author Manuscript, National Institute of Health, Expert Opin Drug Deliv., Apr. 2010; vol. 1, No. 4 (pp. 429-444) 28 pages.

Cao et al., "Clustered burst firing in FMR1 premutation hippocampal neurons: amelioration with allopregnanolone," Human Molecular Genetics, 2012, vol. 21, No. 13, pp. 2923-2935.

Kesisoglou et al., "Utility of PBPK Absorption Modeling to Guide Modified Release Formulation Development of Gaboxadol, a Highly Soluble Compound with Region-Dependent Absorption," Research Article—Pharmaceutics, Drug Delivery and Pharmaceutical Technology, Aug. 19, 2015; Journal of Pharmacetuical Sciences, vol. 105 (2016); pp. 722-728 (7 pages).

Bacalman et al., "Psychiatric Phenotype of the Fragile X-Associated Tremor/Ataxia Syndrome (FXTAS) in Males: Newly Described Fronto-Subcortical Dementia," J. Clinicial Psychiatry, 2006, vol. 67; pp. 87-94.

Jacquemont et al., "Fragile-X syndrome and fragile X-associated tremor/ataxia syndrome: two faces of FMR1," Neurology, The Lancet, vol. 6, Jan. 2007, pp. 45-55.

Berman et al., "Mouse Models of Fragile X-Associated Tremor Ataxia," J. Investig Med., Dec. 2009, vol. 57, No. 3, pp. 837-841. (10 pages).

Entezam et al.., "Regional FMRP deficits and large repeat expansions into the full mutation range in a new Fragile X premutation mouse model," Gene, 2007, vol. 395, No. 1-2, pp. 125-134 (18 pages).

Tassone et al., "Elevated Levels of FMR1 mRNA in Carrier Males: A New Mechanism of Involvement in the Fragile X Syndrome," Am. J. Hum. Genet., 2000, vol. 66; pp. 6-15.

Boyle et al., "Next-day residual effects of gaboxadol and flurazepam administered at bedtime: a randomized double-blind study in healthy elderly subjects," Human Psychopharmacology, 2009, vol. 24, pp. 61-71.

Chaturvedi et al., "Fast Dissolving Films: A Review," Current Drug Delivery, 2011, vol. 8; pp. 373-380.

Ciper and Bodmeier, "Preparation and characterization of novel fast disintegrating capsules (Fastcaps) for administration in the oral cavity," Science Direct, International Journal of Pharmaceutics, 2005, vol. 303; pp. 62-71.

Boateng et al., "Characterisation of freeze-dried wafers and solvent evaporated films as potential drug delivery systems to mucosal surfaces," International Journal of Pharmaceutics, vol. 389, Issues 1-2, Apr. 15, 2010, pp. 24-31.

Journal of Labelled Compounds and Radiopharmaceuticals, 1982, vol. 19, No. 5; pp. 689-702.

Sametsky et al., "Enhanced GABAA—Mediated Tonic Inhibition in AUditgory Thalamus of Rats with Behavioral Evidence of Tinnitus", The Journal of Neuroscience, vol. 35, No. 25, Jun. 24, 2015; pp. 9369-9380.

Richardson et al., "Targeting Inhibitory Neurotransmission in Tinitus", Elsevier, SciVerse ScienceDirect, Brain Research 1485, Feb. 2012; pp. 77-87.

International Search Report and Written Opinion, dated Oct. 31, 2017, corresponding to International Applicaiton No. PCT/US17/46256; 10 total pages.

English translation of Israeli Office Action dated May 14, 2020, corresponding to counterpart Israeli Application No. 256912; 5 pages.

English translation of Taiwanese Search Report dated Mar. 30, 2020, corresponding to counterpart Taiwanese Application No. 105122538; 1 pages.

Japanese Office Action (with English Summary) dated May 12, 2020, corresponding to counterpart Japanese Application No. 2018-502084; 4 total pages.

Thaker et al., "Brain γ-Aminobutyric Acid Abnormality in Tardive Dyskinesia," Archives of General Psychiatry, (1987), vol. 44, No. 6; pp. 522-529.

Chinese Office Action (with cited references in English) dated Mar. 20, 2020, corresponding to counterpart Chinese Application No. 201680054308.1; 11 total pages.

European Communication dated May 7, 2020, corresponding to counterpart European Application No. 16 828 266.3; 6 pages.

\* cited by examiner

METHODS OF TREATING DEVELOPMENTAL DISORDERS WITH GABOXADOL

CROSS REFERENCE TO RELATED APPLICATIONS

This application is a continuation application of U.S. application Ser. No. 16/053,343, filed Aug. 2, 2018, which is a continuation application of U.S. application Ser. No. 15/840,521, filed Dec. 13, 2017, which is a continuation application of U.S. application Ser. No. 15/209,862, filed Jul. 14, 2016, which claims benefit of and priority to U.S. Provisional Application Nos. 62/346,763, filed Jun. 7, 2016, 62/332,567, filed May 6, 2016, 62/207,595 filed Aug. 20, 2015, and 62/193,717, filed Jul. 17, 2015; and U.S. application Ser. No. 16/053,343 filed Aug. 2, 2018, is also a continuation of U.S. application Ser. No. 15/616,460, filed Jun. 7, 2017, which claims benefit of and priority to U.S. Provisional Application No. 62/346,763, filed Jun. 7, 2016, each of which are incorporated herein by reference in their entireties.

TECHNICAL FIELD

Methods of treating developmental disorders with gaboxadol, or a pharmaceutically acceptable salt thereof are provided.

BACKGROUND

Gaboxadol (4,5,6,7-tetrahydroisoxazolo [5,4-c]pyridine-3-ol) (THIP)) is described in EP Patent No. 0000338 and in EP Patent No. 0840601, U.S. Pat. Nos. 4,278,676, 4,362,731, 4,353,910, and WO 2005/094820. Gaboxadol is a selective GABAA receptor agonist with a preference for δ-subunit containing GABAA receptors. In the early 1980s gaboxadol was the subject of a series of pilot studies that tested its efficacy as an analgesic and anxiolytic, as well as a treatment for tardive dyskinesia, Huntington's disease, Alzheimer's disease, and spasticity. In the 1990s gaboxadol moved into late stage development for the treatment of insomnia. The development was discontinued after the compound failed to show significant effects in sleep onset and sleep maintenance in a three-month efficacy study. Additionally, patients with a history of drug abuse who received gaboxadol experienced a steep increase in psychiatric adverse events.

Treatments for developmental disorders such as Autistic Spectrum Disorder, Rett syndrome, Angelman syndrome, and Fragile X syndrome are limited. For example, Angelman syndrome is a neurodevelopmental disorder caused by loss of function of the UBE3A gene encoding a ubiquitin E3 ligase. Motor dysfunction is a characteristic feature of Angelman syndrome, but neither the mechanisms of action nor effective therapeutic strategies have yet been elucidated. Administering low doses of gaboxadol has been shown to improve the abnormal firing properties of a population of Purkinje cells in cerebellar brain slices and reduces cerebellar ataxia in Ube3a-deficient mice in vivo. These results suggest that pharmacologically increasing tonic inhibition may be a useful strategy for alleviating motor dysfunction in Angelman syndrome. Egawa, et al., *Science Translational Medicine*, 4:163ra157 (2012).

Fragile X syndrome may be the most common genetic cause of intellectual disability and the most common single-gene cause of autism. It is caused by mutations on the fragile X mental retardation gene (FMR1) and lack of fragile X mental retardation protein, which in turn, leads to decreased inhibition of translation of many synaptic proteins. The main efforts have focused on metabotropic glutamate receptor (mGluR) targeted treatments; however, investigation on the gamma-aminobutyric acid (GABA) system and its potential as a targeted treatment is less emphasized. The fragile X mouse models (Fmr1-knock out) show decreased GABA subunit receptors, decreased synthesis of GABA, increased catabolism of GABA, and overall decreased GABAergic input in many regions of the brain. These symptoms are also observed in individuals with autism and other neurodevelopmental disorders, therefore the targeted treatments for Fragile X syndrome are leading the way in the treatment of other neurodevelopmental syndromes and autism. Potential GABAergic treatments, such as riluzole, gaboxadol, tiagabine, and vigabatrin have been discussed. However, further studies are needed to determine the safety and efficacy of GABAergic treatments for Fragile X syndrome. Moreover, further studies in fragile X animal models are necessary to provide cumulative evidence in the efficacy and safety of gaboxadol. Lozano et al., Neuropsychiatr Dis Treat.,10: 1769-1779 (2014).

Fragile X-associated tremor/ataxia syndrome (FXTAS) is a late-onset disorder, usually occurring after age 50. Mutations in the FMR1 gene increase the risk of developing FXTAS. The mutation relates to a DNA segment known as a CGG triplet repeat which is expanded within the FMR1 gene. Normally, this DNA segment is repeated from 5 to about 40 times. In people with FXTAS the CGG segment may be repeated 55 to 200 times. This mutation is known as an FMR1 gene premutation. An expansion of more than 200 repeats, a full mutation, causes Fragile X syndrome discussed above. FXTAS is typically characterized by problems with movement and thinking ability (cognition). FXTAS signs and symptoms usually worsen with age. Affected individuals have areas of damage in the cerebellum, the area of the brain that controls movement. Characteristic features of FXTAS are intention tremor, which is trembling or shaking of a limb when trying to perform a voluntary movement such as reaching for an object, and problems with coordination and balance (ataxia). Many affected individuals develop other movement problems, such as parkinsonism, which includes tremors when not moving (resting tremor), rigidity, and unusually slow movement (bradykinesia). In addition, affected individuals may have reduced sensation, numbness or tingling, pain, or muscle weakness in the lower limbs, and inability to control the bladder or bowel. Other symptoms may include chronic pain syndromes, such as fibromyalgia and chronic migraine, hypothyroidism, hypertension, insomnia, sleep apnea, vertigo, olfactory dysfunction, and hearing loss. People with FXTAS commonly have cognitive disabilities such as short-term memory loss and loss of executive function, which is the ability to plan and implement actions and develop problem-solving strategies. Loss of this function impairs skills such as impulse control, self-monitoring, focusing attention appropriately, and cognitive flexibility. Many people with FXTAS experience psychiatric symptoms such as anxiety, depression, moodiness, or irritability.

There is currently no targeted therapeutic intervention that can arrest or reverse the pathogenesis of FXTAS. However a number of treatment approaches of potential symptomatic benefit have been suggested. Primidone, beta-blockers such as propanolol, topiramate, carbidopa/levodopa, and benzodiazepines have been suggested to control tremors associated with FXTAS; botulinum toxin for involuntary muscle activities, such as dystonia and spasticity; carbidopa/levodopa, amantadine and buspirone for ataxia; cholinesterase inhibitors such as donepezil, and memantine (an NMDA antagonist) for cognitive deficits and dementia; and antidepressants and antipsychotics for psychiatric symptoms. See, e.g., Hagerman, et al., Clin Interv Aging. 2008 June; 3(2): 251-262.

Accordingly, there remains a need for effective treatments of patients with for developmental disorders, such as Angelman syndrome, Fragile X syndrome, Fragile X-associated tremor/ataxia syndrome (FXTAS), Autistic Spectrum Disorder, Autism, Asperger's syndrome, pervasive developmental disorder, Childhood Disintegrative Disorder, Rett syndrome, Lanau-Kleffner Syndrome, Prader-Willi Syndrome, Tardive Dyskinesia, and/or Williams Syndrome.

SUMMARY

Methods of treating a developmental disorder described herein include administering to a patient in need thereof about 0.05 mg to about 30 mg gaboxadol or a pharmaceutically acceptable salt thereof wherein the method provides improvement in next day functioning. Methods of treating a developmental disorder including an Autistic Spectrum Disorder, Autism, Angelman syndrome, and Fragile X syndrome by administering to a patient in need thereof gaboxadol or a pharmaceutically acceptable salt thereof, wherein the method provides improvement in next day functioning. Methods of treating a developmental disorder described herein include administering to a patient in need thereof gaboxadol or a pharmaceutically acceptable salt thereof wherein the method provides improvement in the patient for more than 6 hours after administration to the patient. Methods of treating a developmental disorder are described herein which include administering to a patient in need thereof gaboxadol or a pharmaceutically acceptable salt thereof wherein the method provides an in vivo plasma profile including a $C_{max}$ less than about 400 ng/ml and wherein the method provides improvement in the patient for more than 6 hours after administration of the gaboxadol or a pharmaceutically acceptable salt thereof. Methods of treating a developmental disorder are described herein which include administering to a patient in need thereof gaboxadol or a pharmaceutically acceptable salt thereof wherein the method provides an in vivo plasma profile comprising a $AUC_{6-12}$ of less than about 900 ng•hr/ml and wherein the method provides improvement in the patient for more than 6 hours after administration of the gaboxadol or a pharmaceutically acceptable salt thereof. Methods of treating a developmental disorder are described herein which include administering to a patient in need thereof a first pharmaceutical composition comprising gaboxadol or a pharmaceutically acceptable salt thereof and a second pharmaceutical composition comprising gaboxadol or a pharmaceutically acceptable salt thereof wherein the second pharmaceutical composition provides an in vivo plasma profile comprising a mean $AUC_{0-\infty}$ of at least 20% less than the first pharmaceutical composition.

In embodiments, the developmental disorder may be an Autistic Spectrum Disorder, pervasive developmental disorder, Autism, Angelman syndrome, Fragile X syndrome, Fragile X-associated tremor/ataxia syndrome (FXTAS), Rett syndrome, Asperger's syndrome, Childhood Disintegrative Disorder, Lanau-Kleffner Syndrome, Prader-Willi Syndrome, Tardive Dyskinesia, and/or Williams Syndrome.

DETAILED DESCRIPTION

Figure 1:
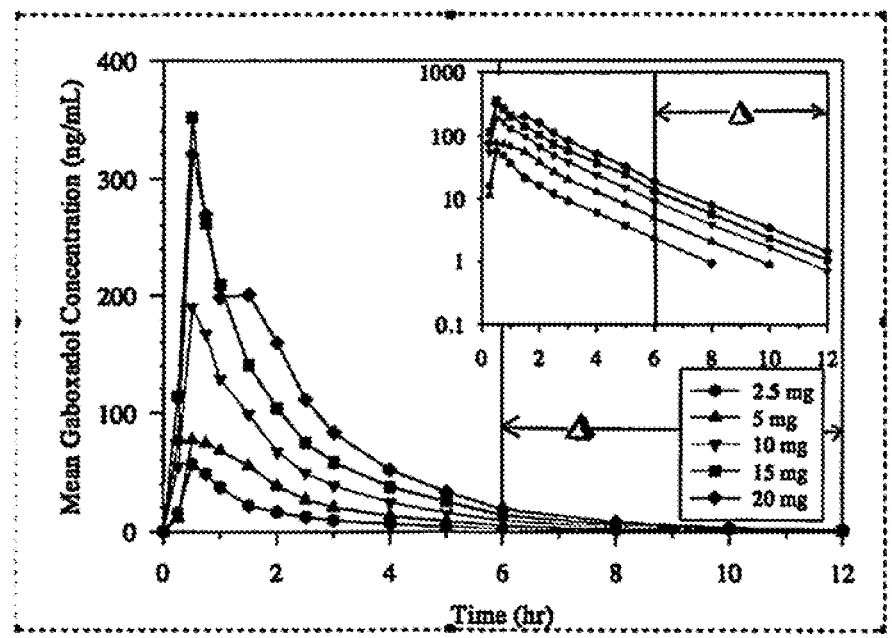
FIG. 1 shows the arithmetic mean plasma concentration-time profiles of gaboxadol following single oral doses (2.5, 5, 10, 15, and 20 mg) as described in Example 1 with horizontal lines A indicating the change between 6 and 12 hours.

Described herein are methods of treating developmental disorders with gaboxadol or a pharmaceutically acceptable salt thereof. Many pharmaceutical products are administered as a fixed dose, at regular intervals, to achieve therapeutic efficacy. Its duration of action is reflected by its plasma half-life. Gaboxadol is a selective GABAA receptor agonist with a relatively short half-life (t½=1.5 h). Since efficacy is often dependent on sufficient exposure within the central nervous system administration of CNS drugs with a short half-life may require frequent maintenance dosing. Advantageously disclosed herein are methods of treating developmental disorders by administration of gaboxadol or a pharmaceutically acceptable salt thereof. For example, in embodiments, methods of treating a developmental disorder are provided which include administering to a patient in need thereof a pharmaceutical composition including about 0.05 mg to about 30 mg gaboxadol or a pharmaceutically acceptable salt thereof wherein the composition provides improvement for more than 6 hours after administration to the patient. In some embodiments, the methods described herein may advantageously be used to provide improvements in the patient for a prolonged period of time after administration of a single dosage (e.g., an evening dosage).

In embodiments, the developmental disorder is an Autistic Spectrum Disorder, pervasive developmental disorder, Autism, Angelman syndrome, Fragile X syndrome, Fragile X-associated tremor/ataxia syndrome (FXTAS), Rett syndrome, Asperger's syndrome, Childhood Disintegrative Disorder, Lanau-Kleffner Syndrome, Prader-Willi Syndrome, Tardive Dyskinesia, and/or Williams Syndrome. In embodiments, the developmental disorder Autism, Rett syndrome, Angelman syndrome, and/or Fragile X syndrome. In embodiments, the developmental disorder is a pervasive developmental disorder not otherwise characterized (PDD-NOS). Symptoms of PDD-NOS can vary widely from one child to the next. Overall, child with PDD-NOS can be characterized as having impaired social interaction, better language skills than children with autistic disorder but not as good as those with Asperger's syndrome, fewer repetitive behaviors than children with Asperger's syndrome or autistic disorder, and a later age of onset.

In embodiments, the developmental disorder is Autism. In other embodiments, the developmental disorder is Angelman syndrome. In embodiments the developmental disorder is Fragile X syndrome. In embodiments the developmental disorder is Fragile X-associated tremor/ataxia syndrome (FXTAS)

Embodiments described herein provide that a patient in need thereof is administered a pharmaceutical composition including gaboxadol or a pharmaceutically acceptable salt thereof. Advantageously disclosed herein are methods of treating developmental disorders by administration of gaboxadol or a pharmaceutically acceptable salt thereof once in the evening to provide improvements in next day functioning of the patient. Gaboxadol or pharmaceutically acceptable salt thereof may be provided as an acid addition salt, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used.

In embodiments, gaboxadol is provided as gaboxadol monohydrate. One skilled in the art will readily understand that the amounts of active ingredient in a pharmaceutical composition will depend on the form of gaboxadol provided. For example, pharmaceutical compositions of including 5.0, 10.0, or 15.0 mg gaboxadol correspond to 5.6, 11.3, or 16.9 mg gaboxadol monohydrate.

In embodiments, gaboxadol is crystalline, such as the crystalline hydrochloric acid salt, the crystalline hydrobromic acid salt, or the crystalline zwitter ion monohydrate. In embodiments, gaboxadol is provided as a crystalline monohydrate.

Deuteration of pharmaceuticals to improve pharmacokinetics (PK), pharmacodynamics (PD), and toxicity profiles, has been demonstrated previously with some classes of drugs. Accordingly the use of deuterium enriched gaboxadol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched gaboxadol. See Journal of Labeled Compounds and Radiopharmaceuticals 19(5) 689-702 (1982).

Deuterium enriched gaboxadol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments deuterium enriched gaboxadol means that the specified position is enriched with deuterium above the naturally occurring distribution (i.e., above about 0.0156%). In embodiments deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

In embodiments methods of treating a developmental disorder include administering to a patient in need thereof a pharmaceutical composition including about 0.05 mg to about 30 mg gaboxadol or a pharmaceutically acceptable salt thereof.

In embodiments, the pharmaceutical compositions include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, 3 mg to 15 mg gaboxadol or a pharmaceutically acceptable salt thereof.

In embodiments, the pharmaceutical compositions include 5 mg to 20 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the pharmaceutical compositions include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the pharmaceutical compositions include 2.5 mg, 5 mg, 7.5 mg, 10 mg, 15 mg, or 20 mg gaboxadol or a pharmaceutically acceptable salt thereof.

Pharmaceutical compositions herein may be provided with immediate release, delayed release, extended release, or modified release profiles. In embodiments, pharmaceutical compositions with different drug release profiles may be combined to create a two-phase or three-phase release profile. For example, pharmaceutical compositions may be provided with an immediate release and an extended release profile. In embodiments, pharmaceutical compositions may be provided with an extended release and delayed release profile. Such composition may be provided as pulsatile formulations, multilayer tablets, or capsules containing tablets, beads, granules, etc. Compositions may be prepared using a pharmaceutically acceptable "carrier" composed of materials that are considered safe and effective. The "carrier" includes all components present in the pharmaceutical formulation other than the active ingredient or ingredients. The term "carrier" includes, but is not limited to, diluents, binders, lubricants, disintegrants, fillers, and coating compositions.

In embodiments, the pharmaceutical compositions described herein are administered once, twice, or three times daily, or every other day. In embodiments, the pharmaceutical compositions described herein are administered once daily. In embodiments, a pharmaceutical composition described herein is provided to the patient in the evening. In embodiments, a pharmaceutical composition described herein is provided to the patient once in the evening and provides improvement in next day functioning of the patient. In embodiments, a pharmaceutical composition described herein is provided to the patient once in the evening and once in the morning. In embodiments, the pharmaceutical compositions described herein are administered three times daily. In embodiments, the total amount of gaboxadol or a pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 5 mg, 10 mg, or 15 mg. In embodiments, the total amount of gaboxadol or a pharmaceutically acceptable salt thereof administered to a subject in a 24-hour period is 20 mg.

In embodiments, provided herein are methods of treating a developmental disorder including administering to a patient in need thereof a pharmaceutical composition including gaboxadol or a pharmaceutically acceptable salt thereof wherein the composition provides improvement in at least one symptom of the developmental disorder. Symptoms may include, but are not limited to, ataxia, gait, speech impairment, vocalization, cognition, motor activity, clinical seizure, hypotonia, hypertonia, feeding difficulty, drooling, mouthing behavior, sleep difficulties, hand flapping, easily provoked laughter and short attention span. In embodiments, provided in accordance with the present disclosure is improvement in cognition. Cognition refers to the mental processes involved in gaining knowledge and comprehension, such as thinking, knowing, remembering, judging, and problem solving. These higher-level functions of the brain encompass language, imagination, perception, and the planning and execution of complex behaviors.

In embodiments, provided herein are methods of treating a developmental disorder including administering to a patient in need thereof a pharmaceutical composition including gaboxadol or a pharmaceutically acceptable salt thereof wherein the composition provides improvement of at least one symptom for more than 4 hours after administration of the pharmaceutical composition to the patient. In embodiments, the improvement of at least one symptom for more than 6 hours after administration of the pharmaceutical composition to the patient is provided in accordance with the present disclosure. In embodiments, improvement of at least one symptom for more than, e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for at least e.g., 8 hours, 10 hours, 12 hours, 15 hours, 18 hours, 20 hours, or 24 hours after administration of the pharmaceutical composition to the patient is provided in accordance with the present disclosure. In embodiments, improvement in at least one symptom for 12 hours after administration of the pharmaceutical composition to the patient is provided in accordance with the present disclosure.

In embodiments, provided herein methods of treating a developmental disorder including administering to a patient in need thereof a pharmaceutical composition including gaboxadol or a pharmaceutically acceptable salt thereof wherein the composition provides improvement in next day functioning to the patient.

FIG. 1 shows the arithmetic mean plasma concentration-time profiles of gaboxadol following single oral doses (2.5, 5, 10, 15, and 20 mg)(see, Example 1, below) with horizontal lines A indicating the change between 6 and 12 hours. In embodiments, provided herein are methods of treating a developmental disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 50% and the method provides improvement in the patient for more than 6, 8, 10, 12, 14, 16, 18, 20, 22 or 24 hours after administration. In embodiments, provided herein are methods of treating a developmental disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 55% and the method provides improvement in the patient for more than 6, 8, 10, 12, 14, 16, 18, 20, 22 or 24 hours after administration. In embodiments, provided herein are methods of treating a developmental disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 60% and the method provides improvement in the patient for more than 6, 8, 10, 12, 14, 16, 18, 20, 22 or 24 hours after administration. In embodiments, provided herein are methods of treating a developmental disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 65% and the method provides improvement in the patient for more than 6, 8, 10, 12, 14, 16, 18, 20, 22 or 24 hours after administration. In embodiments, provided herein are methods of treating a developmental disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 70% and the method provides improvement in the patient for more than 6, 8, 10, 12, 14, 16, 18, 20, 22 or 24 hours after administration. In embodiments, provided herein are methods of treating a developmental disorder including administering to a patient in need thereof about 0.05 mg to about 30 mg gaboxadol or a pharmaceutically acceptable salt thereof which provides an in vivo plasma profile, wherein the in vivo plasma profile of the patient 6 hours after administration of the gaboxadol or pharmaceutically acceptable salt thereof is reduced by more than 75% and the method provides improvement in the patient for more than 6, 8, 10, 12, 14, 16, 18, 20, 22 or 24 hours after administration.

In embodiments, provided herein are methods of treating a developmental disorder wherein the amount of gaboxadol or pharmaceutically acceptable salt thereof within the patient about 4 hours after administration of the pharmaceutical composition is less than about 75% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 75%.

In embodiments, provided herein are methods of treating a developmental disorder wherein the amount of gaboxadol or pharmaceutically acceptable salt thereof within the patient about 4 hours after administration of the pharmaceutical composition is less than about 80% of the administered dose. In embodiments, provided herein are methods wherein the amount of gaboxadol or pharmaceutically acceptable salt thereof within the patient about, e.g., 6 hours, 8 hours, 10 hours, 12 hours, 15 hours, or 20 hours after administration of the pharmaceutical composition is less than about 80% of the administered dose.

In embodiments, provided herein are methods of treating a developmental disorder wherein the amount of gaboxadol or pharmaceutically acceptable salt thereof within the patient about 4 hours after administration of the pharmaceutical composition is between about 65% to about 85% of the administered dose. In embodiments, the amount of gaboxadol or pharmaceutically acceptable salt thereof within the patient after about, e.g., 6 hours, 8 hours, 10 hours, 12 hours, 15 hours, or 20 hours after administration of the pharmaceutical composition is between about 65% to about 85% of the administered dose.

In embodiments, provided herein are methods of treating a developmental disorder including administering to a patient in need thereof a pharmaceutical composition including gaboxadol or a pharmaceutically acceptable salt thereof wherein the composition provides an in vivo plasma concentration 6 hours after administration which is less than 75% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma concentration 6 hours after administration which is less than 80% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma concentration 6 hours after administration which is less than 85% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma concentration 6 hours after administration which is less than 90% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma concentration 6 hours after administration which is less than 95% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma concentration 6 hours after administration which is less than 100% of the administered dose and provides improvement in the patient for more than 6, 8, 10, 12, 14, 16, 18, 20, 22 or 24 hours after administration.

In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $C_{max}$ less than about 500 ng/ml. In embodiments, the composition provides improvement for more than 6 hours after administration to the patient.

In embodiments, the composition provides an in vivo plasma profile having a $C_{max}$ less than about, e.g., 450 ng/ml, 400 ng/ml 350 ng/ml, or 300 ng/ml and wherein the composition provides improvement of next day functioning of the patient. In embodiments, the composition provides an in vivo plasma profile having a $C_{max}$ less than about, e.g., 250 ng/ml, 200 ng/ml 150 ng/ml, or 100 ng/ml and wherein the composition provides improvement of next day functioning of the patient.

In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{0-\infty}$ of less than about 900 ng•hr/ml. In embodiments, the composition provides improvement in next day functioning of the patient. In embodiments, the compositions provide an in vivo plasma profile having a $AUC_{0-\infty}$ of less than about, e.g., 850 ng•hr/ml, 800 ng•hr/ml, 750 ng•hr/ml, or 700 ng•hr/ml and wherein the composition provides improvement of next day functioning of the patient. In embodiments, the composition provides improvement in one or more symptom for more than 6 hours after administration.

In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{0-\infty}$ of less than about, e.g., 650 ng•hr/ml, 600 ng•hr/ml, 550 ng•hr/ml, 500 ng•hr/ml, or 450 ng•hr/ml. In embodiments, wherein the composition provides an in vivo plasma profile having a $AUC_{0-\infty}$ of less than about, e.g., 400 ng•hr/ml, 350 ng•hr/ml, 300 ng•hr/ml, 250 ng•hr/ml, or 200 ng•hr/ml. In embodiments, the composition provides an in vivo plasma profile having a $AUC_{0-\infty}$ of less than about, e.g., 150 ng•hr/ml, 100 ng•hr/ml, 75 ng•hr/ml, or 50 ng•hr/ml. In embodiments, the composition provides improvement of next day functioning of the patient after administration for more than, e.g., 4 hours, 6 hours, 8 hours, 10 hours, or 12 hours, after administration of the composition to the patient.

In embodiments, provided herein are methods of treating a developmental disorder including administering to a patient in need thereof an amount of gaboxadol or a pharmaceutically acceptable salt thereof which provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof an amount of gaboxadol or a pharmaceutically acceptable salt thereof which provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof an amount of gaboxadol or a pharmaceutically acceptable salt thereof which provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof an amount of gaboxadol or a pharmaceutically acceptable salt thereof which provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof an amount of gaboxadol or a pharmaceutically acceptable salt thereof which provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof an amount of gaboxadol or a pharmaceutically acceptable salt thereof which provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 75% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 80% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 85% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 90% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 95% of the $C_{max}$ and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 100% of the $C_{max}$ and provides improvement in the patient for more than 6, 8, 10, 12, 14, 16, 18, 20, 22 or 24 hours after administration.

In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 75% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 80% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 85% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 90% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 95% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a pharmaceutical composition including gaboxadol or a pharmaceutically acceptable salt thereof wherein the composition provides an in vivo plasma profile having a $AUC_{6-12}$ which is less than 100% of the administered dose and provides improvement in the patient for more than 6, 8, 10, 12, 14, 16, 18, 20, 22 or 24 hours after administration. In embodiments, provided herein are methods of treating a developmental disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of at least about 20% less than the first pharmaceutical composition.

In embodiments the first and/or the second pharmaceutical compositions are administered once, twice, or three times daily, or every other day. In embodiments, the first or the second pharmaceutical composition is provided to the patient in the evening. In embodiments, the second pharmaceutical composition includes an amount of gaboxadol that is at least one third of the amount of gaboxadol provided in the first pharmaceutical composition. In embodiments, the second pharmaceutical composition includes an amount of gaboxadol that is at least half of the amount of gaboxadol provided in the first pharmaceutical composition.

In embodiments, the first or the second pharmaceutical composition is provided to the patient once in the evening and once in the morning. In embodiments, the total amount of gaboxadol or pharmaceutically acceptable salt thereof administered to a subject in a 24-hour period is 1 mg to 30 mg. In embodiments, the total amount of gaboxadol or a pharmaceutically acceptable salt thereof administered to a subject in a 24-hour period is 1 mg to 20 mg. In embodiments, the total amount of gaboxadol or a pharmaceutically acceptable salt thereof administered to a subject in a 24-hour period is 10 mg, 15 mg, or 20 mg. In embodiments, the total amount of gaboxadol or a pharmaceutically acceptable salt thereof administered to a subject in a 24-hour period is 20 mg.

In embodiments, the first and/or the second pharmaceutical compositions may be provided with immediate release, delayed release, extended release, or modified release profiles. The first and second pharmaceutical compositions may be provided at the same time or separated by an interval of time, e.g., 6 hours, 12 hours etc. In embodiments, the first and the second pharmaceutical compositions may be provided with different drug release profiles to create a two-phase release profile. For example, the first pharmaceutical composition may be provided with an immediate release profile and the second pharmaceutical composition may provide an extended release profile. In embodiments, one or both of the first and second pharmaceutical compositions may be provided with an extended release or delayed release profile. Such compositions may be provided as pulsatile formulations, multilayer tablets or capsules containing tablets, beads, granules, etc. In some embodiments, the first pharmaceutical composition is an immediate release composition. In embodiments, the second pharmaceutical composition is an immediate release composition. In embodiments, the first and second pharmaceutical compositions are provided as separate immediate release compositions, e.g., tablets or capsules. In embodiments the first and second pharmaceutical compositions are provided 12 hours apart.

In embodiments, provided herein are methods of treating a developmental disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ at least about, e.g., 25%, 30%, 35%, 40%, 45% or 50% less than the first pharmaceutical composition. In embodiments, the composition provides improvement of next day functioning of the patient. For example, the composition may provide improvement in one or more symptoms for more than about, e.g., 6 hours, 8 hours, 10 hours, or 12 hours after administration of the first and/or second pharmaceutical composition.

In embodiments, provided herein are methods of treating a developmental disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the second pharmaceutical composition provides an in vivo plasma profile having a mean $AUC_{0-\infty}$ of less than about 900 ng•hr/ml. In embodiments, the second pharmaceutical composition provides an in vivo plasma profile having a $AUC_{0-\infty}$ of less than about, e.g., 800 ng•hr/ml, 750 ng•hr/ml, 700 ng•hr/ml, 650 ng•hr/ml, or 600 ng•hr/ml. In embodiments, the second pharmaceutical composition provides an in vivo plasma profile having a $AUC_{0-\infty}$ of less than about, e.g., 550 ng•hr/ml, 500 ng•hr/ml, 450 ng•hr/ml, 400 ng•hr/ml, or 350 ng•hr/ml. In embodiments, the second pharmaceutical composition provides an in vivo plasma profile having a $AUC_{0-\infty}$ of less than about, e.g., 300 ng•hr/ml, 250 ng•hr/ml, 200 ng•hr/ml, 150 ng•hr/ml, or 100 ng•hr/ml. In embodiments, the first and second pharmaceutical composition are administered wherein the compositions provide improvement of next day functioning of the patient. In embodiments, the first pharmaceutical composition provides improvement in one or more symptom for more than, e.g., 6 hours, 8 hours or 12 hours after administration of the first pharmaceutical composition.

In embodiments, provided herein are methods of treating a developmental disorder including administering to a patient in need thereof a first pharmaceutical composition including gaboxadol or a pharmaceutically acceptable salt thereof and a second pharmaceutical composition including gaboxadol or a pharmaceutically acceptable salt thereof wherein the first composition provides an in vivo plasma profile with a $C_{max}$ that is more than about 50% greater than the $C_{max}$ provided by the administration of the second pharmaceutical composition. As used herein the $C_{max}$ provided by the administration of the second pharmaceutical composition may or may not include the plasma profile contribution of the first pharmaceutical composition. In embodiments, the administration of the second pharmaceutical composition does not include the plasma profile contribution of the first pharmaceutical composition. In embodiments, the first composition provides an in vivo plasma profile having a $C_{max}$ that is more than about e.g., 60%, 70%, 80%, or 90% greater than the $C_{max}$ provided by the administration of the second pharmaceutical composition.

In embodiments, the $T_{max}$ of the first pharmaceutical composition is less than 3 hours. In embodiments, the $T_{max}$ of the first pharmaceutical composition is less than 2.5 hours. In embodiments, the $T_{max}$ of the first pharmaceutical composition is less than 2 hours. In embodiments, the $T_{max}$ of the first pharmaceutical composition is less than 1.5 hours. In embodiments, the $T_{max}$ of the first pharmaceutical composition is less than 1 hour.

In embodiments, the first pharmaceutical composition provides a dissolution of at least about 80% within the first 20 minutes of administration to a patient in need thereof. In embodiments, the first pharmaceutical composition provides a dissolution of at least about, e.g., 85%, 90% or 95% within the first 20 minutes of administration to a patient in need thereof. In embodiments, the first pharmaceutical composition provides a dissolution of at least 80% within the first 10 minutes of administration to a patient in need thereof.

In embodiments the first and/or the second pharmaceutical compositions are sub therapeutic dosages. A sub therapeutic dosage is an amount of gaboxadol pharmaceutically acceptable salt thereof that is less than the amount required for a therapeutic effect. In embodiments, a sub therapeutic dosage is an amount of gaboxadol pharmaceutically acceptable salt thereof that alone may not provide improvement in at least one symptom of the developmental disorder but is sufficient to maintain such improvement. In embodiments, the methods provide administering a first pharmaceutical composition that provides improvement in at least one symptom of a developmental disorder and a second composition that maintains the improvement. In embodiments, after administration of the first pharmaceutical composition the second pharmaceutical composition may provide a synergistic effect to improve at least one symptom of a developmental disorder. In embodiments the second pharmaceutical composition may provide a synergistic effect to improve at least one symptom of a developmental disorder.

In embodiments, provided herein are methods of treating a developmental disorder including administering to a patient in need thereof a pharmaceutical composition including a first pharmaceutical dosage including gaboxadol or a pharmaceutically acceptable salt thereof wherein the composition provides improvement for more than 6 hours after administration and a second pharmaceutical composition including a sub therapeutic dosage of gaboxadol or a pharmaceutically acceptable salt thereof.

Administration of the first and second pharmaceutical compositions may be separated by an interval of time to achieve long-term improvement in at least one symptom. In embodiments, the first and second pharmaceutical composition may be administered 6 hours apart. In embodiments the first and second pharmaceutical composition may be administered 12 hours apart. In embodiments, the first and second pharmaceutical compositions may administered within, e.g., 6 hours, 12 hours, 18 hours, 24 hours etc. In embodiments, the first and second pharmaceutical compositions may administered separated by at least, e.g., 6 hours, 12 hours, 18 hours, 24 hours etc. In embodiments, improvement in at least one symptom of a developmental disorder for more than 8 hours after administration to the patient is provided. In embodiments, improvement for more than about, e.g., 10 hours, 12 hours, 15 hours, 18 hours, 20 hours, or 24 hours after administration to the patient is provided.

In embodiments, the first pharmaceutical composition and/or the second pharmaceutical composition include about 0.1 mg to about 40 mg gaboxadol or a pharmaceutically acceptable salt thereof. The amount of gaboxadol or a pharmaceutically acceptable salt thereof in the first pharmaceutical composition and the second pharmaceutical composition may be the same or different. In embodiments, the administration of the first and second pharmaceutical composition may provide a synergistic effect to improve at least one symptom of a developmental disorder.

In embodiments, the first and/or the second pharmaceutical composition include 0.1 mg to 25 mg, 0.1 mg to 20 mg, 0.1 mg to 15 mg, 0.5 mg to 25 mg, 0.5 mg to 20 mg, 0.5 to 15 mg, 1 mg to 25 mg, 1 mg to 20 mg, 1 mg to 15 mg, 1.5 mg to 25 mg, 1.5 mg to 20 mg, 1.5 mg to 15 mg, 2 mg to 25 mg, 2 mg to 20 mg, 2 mg to 15 mg, 2.5 mg to 25 mg, 2.5 mg to 20 mg, 2.5 mg to 15 mg, 3 mg to 25 mg, 3 mg to 20 mg, or 3 mg to 15 mg gaboxadol or a pharmaceutically acceptable salt thereof.

In embodiments, the first and/or the second pharmaceutical composition include 5 mg to 15 mg, 5 mg to 10 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg gaboxadol or a pharmaceutically acceptable salt thereof.

In embodiments, the first and/or the second pharmaceutical composition include 0.1 mg, 0.25 mg, 0.5 mg, 1 mg, 2.5 mg, 3 mg, 4 mg, 5 mg, 7 mg, 7.5 mg, 10 mg, 12.5 mg, 15 mg, 17.5 mg, 20 mg gaboxadol or a pharmaceutically acceptable salt thereof or amounts that are multiples of such doses. In embodiments, the first pharmaceutical compositions include 2.5 mg, 5 mg, 7.5 mg, 10 mg, 15 mg, or 20 mg gaboxadol or a pharmaceutically acceptable salt thereof. In embodiments, the second pharmaceutical compositions include 2.5 mg, 5 mg, 7.5 mg, 10 mg, 15 mg, or 20 mg gaboxadol or a pharmaceutically acceptable salt thereof.

Unless defined otherwise, all technical and scientific terms used herein have the same meanings as commonly understood by one of skill in the art to which the disclosure herein belongs.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and/or up to 1% of a given value. Alternatively, particularly with respect to biological systems or processes, the term can mean within an order of magnitude, preferably within 5-fold, and more preferably within 2-fold, of a value.

"Improvement" refers to the treatment of a developmental disorder measured relative to at least one symptom.

"Improvement in next day functioning" or "wherein there is improvement in next day functioning" refers to improvement wherein the beneficial effect of at least one symptom lasts over a period of time, e.g., 6 hours, 12 hours, 24 hours etc.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng•hr/ml). The area under the curve is governed by clearance. Clearance is defined as the volume of blood or plasma that is totally cleared of its content of drug per unit time (ml/min).

"Treating" or "treatment" refers to alleviating or delaying the appearance of clinical symptoms of a disease or condition in a subject that may be afflicted with or predisposed to the disease or condition, but does not yet experience or display clinical or subclinical symptoms of the disease or condition. In certain embodiments, "treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" also refers to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Pharmaceutically acceptable" refers to molecular entities and compositions that are "generally regarded as safe"-e.g., that are physiologically tolerable and do not typically produce an allergic or similar untoward reaction, such as gastric upset and the like, when administered to a human. In embodiments, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

"Effective amount" or "therapeutically effective amount" means a dosage sufficient to alleviate one or more symptoms of a disorder, disease, or condition being treated, or to otherwise provide a desired pharmacological and/or physiologic effect.

"Patient in need thereof" may include individuals that have been diagnosed with a developmental disorder including, for example, Autism, Angelman's syndrome, Fragile X syndrome, Fragile X-associated tremor/ataxia syndrome (FXTAS), or Rett's syndrome. The methods may be provided to any individual including, e.g., wherein the patient is a neonate, infant, a pediatric patient (6 months to 12 years), an adolescent patient (age 12-18 years) or an adult (over 18 years).

EXAMPLES

The Examples provided herein are included solely for augmenting the disclosure herein and should not be considered to be limiting in any respect.

mg gaboxadol capsule and 1 matching placebo capsule; and Treatment E—20 mg gaboxadol (two 10 mg gaboxadol capsules). Subjects received their study drug after an overnight fast with 240 mL of water in the morning about 8:00 AM. Water was permitted ad libitum except within 1 hour prior to and after study drug administration. No food was allowed for 4 hours post dose.

For each subject in each treatment, plasma and urine samples were collected over 16 hours post-dosing for the determination of pharmacokinetic parameters (e.g., AUC, $C_{max}$, $T_{max}$, apparent $t_{1/2}$, cumulative urinary excretion, renal clearance, clearance, and steady-state volume of distribution, as appropriate). AUC and $C_{max}$ for gaboxadol were potency adjusted to facilitate comparison of pharmacokinetic data across studies. Table I provides the individual potency-adjusted pharmacokinetic parameters of gaboxadol following single oral doses (2.5, 5, 10, 15, and 20 mg).

TABLE I

Pharmacokinetic parameters for gaboxadol following oral and IV administration

| | Geometric Mean (N = 10) | | | | | | |
|---|---|---|---|---|---|---|---|
| Parameter | 2.5 mg | 5 mg | 10 mg Oral | 10 mg I.V. | 15 mg | 20 mg | Slope (90% CI) [††] |
| $AUC_{0-\infty}$ (ng · hr/mL) | 90 | 171 | 346 | 380 | 539 | 669 | 0.98 (0.95, 1.01) |
| $C_{max}$ (ng/mL)[†] | 61 | 110 | 232 | 212 | 382 | 393 | 0.95 (0.88, 1.02) |
| $T_{max}$ (hr)[‡] | 0.5 | 0.6 | 0.5 | — | 0.5 | 0.6 | |
| Apparent $t_{1/2}$ (hr)[§] | 1.5 | 1.5 | 1.6 | 1.5 | 1.5 | 1.6 | |
| CL/F (mL/min)[ѳ] | 461 | 488 | 476 | 438 | 469 | 499 | |
| $F_e$ (%) | 43 | 45 | 53 | 53 | 50 | 53 | |
| $CL_R$ (mL/min) | 196 | 222 | 250 | 208 | 234 | 265 | |
| F (%) (90% CI)[#] | | | | 92% (0.86, 0.97) | | | |

[†]$C_{ooi}$ (ng/mL) for 10 mg. IV.
[‡]Median.
[§]Harmonic Mean.
[ѳ]CL (mL/min) for 10 mg IV.
[#]Bioavailability relative to 10 mg I.V. reference based on pooled dose-adjusted (to 10 mg) oral $AUC_{0-\infty}$ values.
[††] Dose proportionality assessment of oral treatment only.

Example 1

The following Example provides the plasma concentration profiles and dose proportionality of gaboxadol monohydrate following single oral doses ranging from 2.5 to 20 mg. The absolute bioavailability of gaboxadol monohydrate capsules ranging from 2.5 to 20 mg is also assessed.

This study was composed of separate groups of 10 healthy adult subjects (at least 4 of each gender) who participated in a 6-period, double-blind, randomized, crossover study designed to access the dose proportionality and absolute bioavailabilty of 5 single oral doses of gaboxadol across the dose range of 2.5 to 20 mg. The order in which the subjects received the 5 single oral doses of gaboxadol (2.5; 5; 10; 15; and 20 mg) was randomized within Treatment Periods 1 through 5. Each subject was expected to complete all 6 treatment periods and there was a washout of at least 4 days between each treatment period.

Each oral dosing within Treatment Periods consisted of 2 capsules of test drug taken simultaneously at each scheduled dosing. The treatment designations for the orally administered study drugs were as follows: Treatment A—one 2.5 mg gaboxadol capsule and 1 matching placebo capsule; Treatment B—one 5 mg gaboxadol capsule and 1 matching placebo capsule; Treatment C—one 10 mg gaboxadol capsule and 1 matching placebo capsule; Treatment D—one 15

Figure 2:
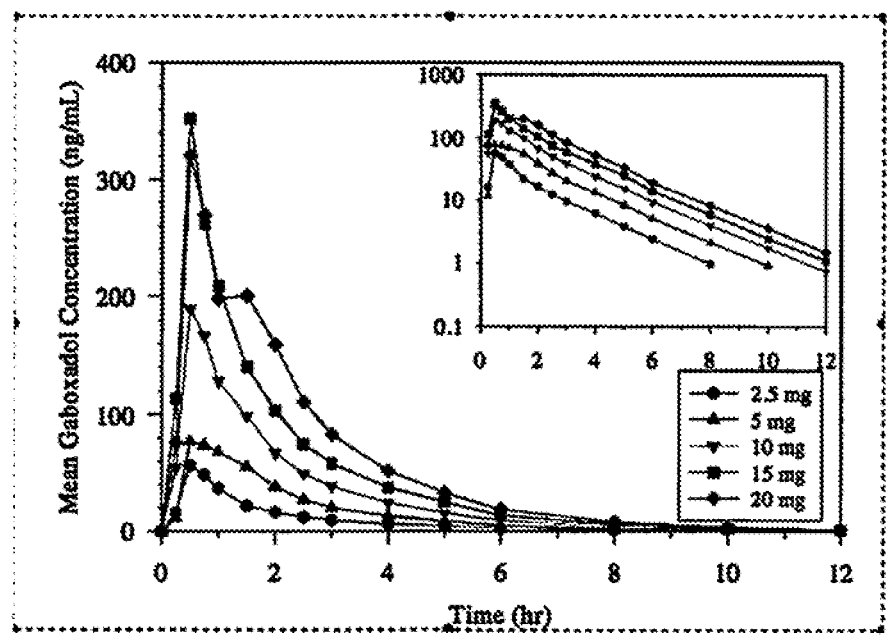
FIG. 2 shows the arithmetic mean plasma concentration-time profiles of gaboxadol following single oral doses (2.5, 5, 10, 15, and 20 mg) as described in Example 1.

FIG. 2 shows the arithmetic mean plasma concentration-time profiles of gaboxadol following single oral doses (2.5, 5, 10, 15, and 20 mg). The bioavailability of gaboxadol is approximately 92%. Plasma $AUC_{0-\infty}$ and $C_{max}$ of gaboxadol show dose proportional increases and appear to be linear over the entire dose range examined, from of 2.5 to 20 mg. The time to peak plasma concentrations ($T_{max}$ 30-60 min) and the half-life (t½ of 1.5 h) for gaboxadol appear to be independent of dose across the gaboxadol dose range of 2.5 to 20 mg. The excretion of gaboxadol is mainly via urine, where 96.5% of the dose is recovered; 75% is recovered within 4 hours after administration.

Example 2

Assessment of Residual Effects Resulting From Gaboxadol Administration

This study was a double blind, double-dummy, randomized, active- and placebo-controlled, single dose, 3-period crossover study, followed by an open-label, single-dose, single period study in healthy elderly male and female subjects. Subjects were randomized to each of 3 treatments (Treatments A, B, and C) to be administered in a crossover manner over the first 3 treatment periods. For Treatment A, subjects received a single dose of gaboxadol 10 mg; for Treatment B, subjects received a single dose of flurazepam 30 mg; and for Treatment C, subjects received a single dose of placebo. Doses were administered orally at bedtime on Day 1. Subjects were domiciled from early in the evening of dosing until ~36 hours post-dose (morning of Day 3) during each treatment period. The subjects who participated in treatment periods 1-3 participated in a fourth treatment period. In this period, a single dose of gaboxadol 10 mg (Treatment D) was administered orally in an open-label manner on the morning of Day 1 for PK of gaboxadol. There was at least a 14-day washout between the doses of consecutive treatment periods. Study participants included healthy, elderly male and female subjects between 65 and 80 years of age, with a Mini Mental Status 24, weighing at least 55 kg. All subjects received 10 mg gaboxadol monohydrate capsules and 30 mg flurazepam (provided as 2×15 mg capsules), matching placebo was provided for both gaboxadol and flurazepam.

The primary endpoints evaluated included pharmacodynamics (measurement of psychomotor performance, memory, attention and daytime sleepiness the following pm dosing), gaboxadol pharmacokinetics, and safety. Gaboxadol (single dose 10 mg) did not show residual effect 9 hours post-dose on the primary endpoints Choice Reaction Time and Critical Flicker Fusion, whereas the active reference Flurazepam (30 mg single dose) showed significant effect on the same tests. In addition, gaboxadol did not show any signs of residual effects on other measurements applied in the study (Multiple Sleep Latency Test (MSLT); Digit symbol substitution test (DSST), Tracking, Memory tests, Body Sway, and Leeds Sleep Evaluation Questionnaire).

Example 3

Study of Driving Performance After Gaboxadol Administration

This study was a double blind, randomized, placebo and active controlled 5 way cross over study to investigate the effect of evening and middle of the night dosing of gaboxadol on driving performance. The study participants included healthy, male and female subjects between 21 and 45 years of age, with a valid drivers license for at least 3 years.

The effects of gaboxadol on driving performance were investigated using real driving on the road setting. Subjects received 15 mg gaboxadol either in the evening prior to going to bed or at 4 am in the middle of the night following a wake-up call. Following a cognitive and psychomotor test battery, the driving test started at 9 am and lasted for one hour. Gaboxadol 15 mg had a clinically relevant impairing effect on driving following middle-of-the-night administration.

Following the evening dose, a statistically significant effect of gaboxadol 15 mg was observed on driving. However, this effect was less than the effect observed at a 0.05% blood alcohol concentration, the concentration limit at which driving is prohibited in most European countries. There was generally a numerically greater effect following zopiclone (7.5 mg) and zolpidem (10 mg) administered in the evening and in the middle of the night, respectively. Both the evening and the middle-of-the-night dose of gaboxadol were well tolerated with the most frequent adverse events being dizziness, nausea and somnolence for the middle-of-the-night treatment and headache and somnolence for the evening treatment.

Subjects on the active reference zopiclone had a numerically greater effect in the same test. There was no effect on memory test, body sway, DSST or critical tracking, whereas zopiclone had effect on several of these tests.

Example 4

Study of Daytime Performance After Sleep Restriction

This study was a 4-night, parallel-group, randomized, double-blind (with in-house blinding), placebo-controlled, fixed-dose study to assess the effects of gaboxadol on daytime performance in healthy adults subjected to a 5-hour sleep restriction. The study included a 2-night single-blind placebo run-in period, a 4-night double-blind treatment period during which sleep was restricted to 5 hours and a 2-night single-blind placebo run-out period. The study included healthy male and female volunteers 18 to <55 years of age.

2-night run-in period: All patients received placebo
4-night double-blind treatment period Patients were randomized to gaboxadol 15 mg or matching placebo
2-night run-out period: All patients received placebo The primary endpoints included observations based on the Multiple Sleep Latency Test (MSLT) and Slow Wave Sleep (SWS) assessment. The primary objective was to evaluate the efficacy of gaboxadol (15 mg) compared to placebo in reducing daytime sleep propensity as measured by MSLT. The gaboxadol subjects had significantly less daytime sleepiness during the Sleep Restriction period than did placebo subjects (p=0.047, 1 sided). The MSLT was on average 2.01 minutes longer for subjects treated with gaboxadol (15 mg) than for those with placebo on the last two Sleep Restriction days.

In addition, a secondary objective was to evaluate the efficacy of gaboxadol compared to placebo in increasing the amount of slow wave sleep (SWS) during the last 2 nights of sleep restriction. Subjects receiving gaboxadol experienced significantly more SWS during the Sleep Restriction period than did placebo subjects (p<0.001, 1 sided). Moreover, subjects treated with gaboxadol on average had 20.53 minutes of SWS longer than those treated with placebo on the last two Sleep Restriction nights.

Finally, this study examined the efficacy of gaboxadol compared to placebo during the last 2 nights/days of sleep restriction in: (1) improving memory and attention as assessed by a neurobehavioral battery; (2) reducing subjective sleepiness as measured by the Karolinska Sleepiness Score (KSS); (3) altering sleep parameters (e.g., total sleep time, latency to onset of Slow Wave Sleep (SWS), slow wave activity (SWA); and (4) reducing biological stress typified by increased heart rate variability, and decreased cortisol levels and decreased catecholamine levels, as well as decreased body temperature.

There was a trend towards less subjective daytime sleepiness for the gaboxadol subjects during the Sleep Restriction period as compared with placebo subjects. The Karolinska Sleepiness Score (KSS) was on average 0.68 less for subjects treated with gaboxadol than for those treated with placebo on the last two Sleep Restriction days (p=0.058, 1 sided) as evaluated by a Longitudinal data analysis (LDA) model with adjustment for baseline KSS, gender, and age. A supportive analysis using covariance (ANCOVA) also supports this finding. The effect sizes computed for the neuro-cognitive battery showed that there was no strong evidence that gaboxadol improves daytime performance. There were no differences between gaboxadol and placebo with respect to biophysiological measures of stress (heart rate variability, cortisol levels, catecholamine levels, body temperature).

Compared with placebo, gaboxadol has a protective effect on reducing daytime sleepiness as measured by the MSLT on the last 2 days of 4-nights of sleep restriction. Compared with placebo, gaboxadol increases the amount of slow wave sleep (SWS) during the last 2 nights of 4-nights of sleep restriction.

Example 5

Assessment of the Efficacy of Gaboxadol in Patients With Angelman Syndrome

This study was designed to determine whether gaboxadol will lead to an improvement in key symptoms of Angelman syndrome (gross and fine motor function, sleep, and behavior problems) and related impact on daily life using questionnaires, diaries, or actimetry data. This multicenter, randomized, parallel (3-arm), double-blind, placebo-controlled trial enrolled 88 patients including adults (n=66) and adolescents (n=22) aged 13 to 49 years of age, diagnosed with Angelman syndrome. The study was designed to evaluate the safety and tolerability of gaboxadol from Baseline to Week 6 and Week 12 in subjects with Angelman syndrome across different dose levels and in 2 dosing schedules. The dosing schedules that were assessed against placebo were once daily (QD): An evening dose titrated to the target dose of 15 mg unless not tolerated; and twice daily (BID): Evening and morning doses titrated to the target doses of 15 mg evening dose and 10 mg morning dose unless not tolerated. Accordingly, the three arms evaluated included (1) once-daily (QD) dose of gaboxadol at night (15 mg); (2) twice daily (BID) dose of gaboxadol (10 mg in the morning and 15 mg at night); and (3) placebo The Clinical Global Impressions (Severity [CGI-S] and Improvement [CGI-I]) were used to assess the efficacy of gaboxadol in subjects. CGI-S scale assessed all sub-domains of Angelman syndrome (gross and fine motor ability, sleep, and adaptive behavior) plus globally by the investigator. On the CGI-S, significant changes for the QD (vs. Placebo) were observed for Stereotypic behavior 3.7 to 3.1 (3.3 to 3.6) and Hyperactivity 3.5 to 2.9 (3.1 to 3.0). The Clinical Global Impressions-Improvement (CGI-I) scale was used to assess all sub-domains of Angelman syndrome (gross and fine motor ability, sleep, and adaptive behavior) plus globally by the investigator and caregiver. CGI-I is a 7-point scale in which the investigator rates the improvement or worsening of symptoms compared to baseline. Once daily dosing (QD) resulted in a CGI-I of 3.0 vs. 3.8 in the placebo group ($p=0.0006$). The CGI-I, as assessed by clinicians, are provided in Table II. The data also shows significant results ($p=0.01$) in the pre-specified primary efficacy endpoint of Angelman syndrome in the combined treatment groups.

In addition, the number of responders (defined by a one point or greater improvement in the CGI-I scale) in overall symptoms in the once daily dose cohort (vs. placebo) was 70% (vs. 26%), increasing from 60% (vs. 22%) in the 25-49 year old, to 73% (vs. 27%) in the 18-24 year old, to 83% (vs. 29%) in the 13-17 year old cohort. Moreover, the percentage who were very much improved on CGI-I in the QD group vs placebo went from 20% (vs. 11%) to 27% (vs. 9%) to 33% (vs. 0%) progressing from the oldest to youngest cohorts. The improvement also increased with duration of treatment, comparing the 6-week to 12-week data.

TABLE II

|  | Placebo (N = 29) | QD dosing (N = 29) | BID dosing (N = 29) | Combined (N = 58) |
| --- | --- | --- | --- | --- |
| 6-week LS Mean | 3.60 (0.15) | 3.54 (0.16) | 3.54 (0.16) | 3.45 (0.12) |
| 6-week LS Mean difference |  | −0.24 (0.21) | −0.06 (0.21) | −0.15 (0.18) |
| 12-week LS Mean | 3.79 (0.16) | 3.00 (0.16) | 3.58 (0.16) | 3.29 (0.12) |
| 12-week LS Mean difference |  | −0.78 (0.22) | −0.21 (0.22) | −0.49 (0.19) |
| P-value* |  | 0.0006 | 0.3446 | 0.010 |

Note:
Subjects are analyzed according to their randomized treatment.
2: CGI-I consists of 10 items. For improvement, scoring is: 1 = very much improved, 2 = much improved, 3 = minimally improved, 4 = no change, 5 = minimally worse, 6 = much worse, 7 = very much worse.
3: A mixed model repeated measures (MMRM) analysis was performed including fixed effects for visit, treatment, age group 1 (adolescent vs. adult), and the visit by treatment interaction using a Unstructured covariance structure.
*Two-sided p-value for the difference of active treatment minus placebo.

The most notable change from patient sleep diaries was in the number of nights slept independently. In the QD dose cohort, one quarter of patients slept every night with parents, at 12 weeks, this had improved to only 1 in 5 nights; in the placebo group, the most effected quarter slept 3 of 4 nights with parents, which had improved to 2 of 4 nights at 12 weeks ($P<0.001$, Chi Square). The observed and change from baseline in total hours of sleep time at night (assessed from subject Sleep Diary) is provided in Table III.

TABLE III

|  | Placebo (N = 29) | QD dosing (N = 29) | BID dosing (N = 29) | Combined (N = 58) |
| --- | --- | --- | --- | --- |
| 6-week LS Mean sleep time | 8.89 (1.4) | 8.91 (1.5) | 8.95 (1.1) | 8.93 (1.3) |
| 6-week LS Mean difference |  | 0.14 (0.81) | 0.30 (1.1) | 0.22 (0.94) |
| 12-week LS Mean sleep time | 8.47 (1.4) | 8.76 (1.2) | 8.84 (1.1) | 8.80 (1.1) |
| 12-week LS Mean difference |  | −0.04 (1.1) | 0.18 (0.97) | 0.07 (1.0) |

Note:
Subjects are analyzed according to their randomized group.
2: Subject daily averages are calculated for Baseline, Week 6, and Week 12 visits using a window of 7 consecutive days prior to each visit. Summary statistics are reported using the daily average for each subject.
3: Total Sleep Time at night is defined from time of sleep onset to time of awakening. Daytime Sleepiness is duration of napping from the daytime sleep diary.

Of particular significance was that treatment-related gastrointestinal adverse events, including nausea, vomiting and abdominal pain, was observed in 6 of 29 placebo patients and 0 of 29 in the once daily gaboxadol group, consistent with improvement in gastrointestinal symptoms in this population ($P<0.01$; Chi-square). Gastrointestinal adverse events may be considered fundamental to the behavioral disturbances seen in autistic spectrum disorders, such as autism and Angelman syndrome. The incidences of treatment-related and treatment-emergent Adverse Events were evaluated by system organ class with those related to gastrointestinal events are provided in Table IV.

TABLE IV

|  | Placebo (N = 29) | QD dosing (N = 29) | BID dosing (N = 29) | Combined (N = 58) |
| --- | --- | --- | --- | --- |
| At least 1 Adverse Event | 13 (45%) | 18 (62%) | 19 (66%) | 37 (64%) |
| Gastrointestinal disorders | 6 (20%) | 0 | 4 (13.8%) | 4 (6.9%) |
| Nausea | 2 (6.9%) | 0 | 2 (6.9%) | 2 (3.4%) |
| Vomiting | 3 (10.3%) | 0 | 1 (3.4%) | 1 (1.7%) |
| Diarrhea | 2 (6.9%) | 0 | 1 (3.4%) | 1 (1.7%) |
| Abdominal Pain upper | 1 (3.4%) | 0 | 0 | 0 |
| Retching | 0 | 0 | 1 (3.4%) | 1 (1.7%) |

Note:
Subjects were analyzed according to their actual treatment.
2: All adverse events are codes using MedDRA version 19.1.
3: A subject is counted only once within each system organ class and preferred term Example 6

Prospective Assessment of the Efficacy of Gaboxadol in Patients With Angelman Syndrome This study is designed to determine whether gaboxadol will lead to an improvement in one or more symptoms of Angelman syndrome. Participants are randomized into 6 separate treatment groups (A-F). Inclusion criteria for randomization will require that each participant has been previously diagnosed with Angelman syndrome by clinical evaluation or that the participant is diagnosed with one or more of the major and minor criteria for Angelman syndrome.
  Major Criteria include:
  Functionally severe developmental delay
  Speech impairment; none or minimal words used
  Movement or balance disorder
  Behavioral uniqueness, frequent laughs/smiling, excitable personality, hand flapping, short attention span
  Minor Criteria include:
  Deceleration in head circumference growth (post-natal)
  Seizures (myoclonic, absence, drop, tonic-clonic)
  Abnormal EEG (with patterns suggestive of AS, or hypsarrhythmia)
  Sleep disturbance
  Attraction to or fascination with water
  Drooling After randomization the participants are placed into 6 separate treatment groups (A-F) and a placebo group. Treatment group A receives 20 mg gaboxadol in the evening. Treatment group B receives 15 mg gaboxadol in the evening. Treatment group C receives 15 mg gaboxadol in the evening and 5 mg gaboxadol in the morning. Treatment group D receives 10 mg gaboxadol in the evening. Treatment group E receives 10 mg gaboxadol in the evening and 10 mg gaboxadol in the morning. Treatment group F receives 10 mg gaboxadol in the evening and 5 mg gaboxadol in the morning.

Participants are assessed throughout the treatment period to determine whether gaboxadol administration leads to an improvement in one or more symptoms of Angelman syndrome. Several behavioral domains; communication, attention, maladaptive behaviors, and hyper-excitability are assessed. To quantify the communication behavior, participants engage in an unstructured play session to elicit speech and non-verbal communication attempts. Speech attempts by the child are transcribed phonetically and categorized into five different types of vocalizations using the Stark Assessment of Early Vocal Development-Revised (SAEVD-R) (Nathani, Ertmer et al. 2006) which categorizes non-speech and pre-speech sounds (protophones), as well as vowels, consonants and syllables.

Gait abnormalities occur in most cases of Angelman syndrome. Thus, five primary spatiotemporal parameters are analyzed: cadence, gait velocity, stride width, step length and percent stance. For each parameter, a principal component analysis is used to establish a gait index for assessment of the subjects.

In addition, primary outcome measures that may be assessed include changes in raw or standard scores between baseline and after trial completion of:
  Bayley Scales of Infant and Toddler Development, 3rd edition (or the Mullen Scales of Early Learning in the more developmentally advanced subjects);
  II. Vineland Adaptive Behavior Scales, 2nd edition (standard scores only);
  III. Preschool Language Scale, 4th edition;
  IV. Aberrant Behavior Checklist—Community version; and
  V. A change from baseline in the Clinical Global Impressions Severity Scale Score.

Secondary outcome measures may include normalization of the electroencephalogram (EEG) signature when comparing post gaboxadol administration results to baseline results.

Example 7

Prospective Assessment of the Efficacy of Gaboxadol in Patients With Angelman Syndrome This study is designed to determine whether gaboxadol leads to an improvement in one or more symptoms of Angelman syndrome (AS). Angelman syndrome manifests as several distinct characteristics that range in severity and include developmental delay, movement and/or balance disorder, and tremulous movement of limbs. Perhaps the most unique behavioral characteristic is the combination of a happy demeanor, smiling and frequent of bouts of laughter. Moreover, these individuals possess an easily excitable personality exhibited by hand-flapping or waving movements. Finally, these individuals suffer from severe disruptions in sleep, impairments in speech, and frequent seizures with characteristic abnormal electroencephalogram (EEG) patterns. All main domains of symptoms of AS (sleep, gross and fine motor function, behavior and communication) will be investigated, using appropriate questionnaires, diaries or actimetric data. Main focus may include motor ability and sleep. Well-established scales may be used, complemented by more innovative outcome measures for sleep and motor function. A potential confounding factor for behavior in AS is the co-existence of autism (Peters et al., Clin Genet, 2004;66[6]:530-6). At Screening, subjects may be assessed for this co-morbidity, using the Autism Diagnostic Observation Schedule (ADOS), and potentially excluded.

The primary objective of this study may be to evaluate the safety and tolerability from Baseline to Week 6 and Week 12 of gaboxadol in adult subjects with AS across different dose levels and in two dosing schedules. The following dosing schedules may be tested against placebo: (1) Once daily (o.d.): An evening dose, titrated to the target dose of 15 mg unless not tolerated; and (2) Twice daily (b.i.d.): Evening and morning doses titrated to the target doses of 15 mg evening dose and 10 mg morning dose unless not tolerated.

The Safety endpoints that relate to this study may include: (1) Frequency and severity of adverse events (AEs) and serious adverse events; (2) Vital signs (weight, blood pressure, temperature); (3) Laboratory parameters (electrolytes, lipids, glucose, liver and pancreas function tests, hematology, creatinine); (4) Suicidality assessed by ABC-Irritability Subscale; (5) EEG (change in background frequency, intensity of epileptiform discharges); and/or (6) Caregivers may maintain an electronic seizure diary (on same device as sleep log).

The secondary objective of this study may include the identification of a set of parameters that may best characterize the efficacy of gaboxadol in adult AS subjects for subsequent efficacy trials. These tests may be administered at four full day site visits (Screening, Baseline, Interim and End of Treatment) by an appropriately trained professional to provide the test to an adult AS patient. Assessments may be based on direct observation and input from caregivers. The efficacy assessments that may be explored include Gross Motor Ability/Function and Fine Motor Ability/Function. Evaluation of Gross Motor Ability/Function may include analysis of spatiotemporal and functional gait measurements (Zeno Walkway and PKMAS software analysis, provided by ProtoKintetics) and Modified Performance Oriented Mobility Assessment-Gait (MPOMA-G) scale assessed while subject is walking on Zeno Walkway. Evaluation of Fine Motor Ability/Function may include analysis of Pediatric Evaluation of Disability Inventory (PEDI-CAT); ADL (to document fine motor function) and mobility domains in the content-balanced (more extensive) version.

This study may include three treatment groups. For example, a total of approximately 75 subjects may be enrolled and at the completion of the study, there may be approximately 25 subjects in each of the three treatment groups: 1) single evening dose 2) morning and evening dose and 3) placebo.

Figure 3:
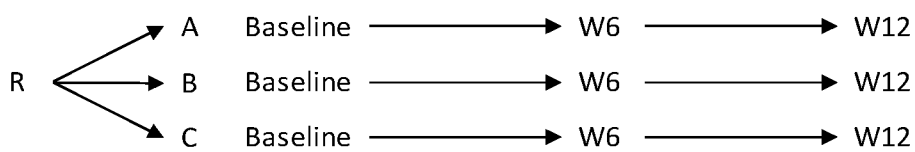
FIG. 3 schematically illustrates treatment of three groups over a proposed 12 week course of treatment: 1) single evening dose 2) morning and evening dose and 3) placebo.

All subjects may receive a morning dose (either active or placebo) and an evening dose (either active or placebo) during the entire duration of treatment. For example, as illustrated in FIG. 3, two dosing schedules of gaboxadol may be tested: a single evening dose (o.d.; Schedule A) and a morning plus evening dose (b.i.d; Schedule B) designed to provide a more sustained exposure. Schedule C is morning and evening placebo. All subjects may be up-titrated to the target dose unless this target dose is not tolerated (titration conventions described below). All subjects may receive treatment for a maximum of 12 weeks at their optimal tolerated dose.

Doses may be progressively increased in 5 mg increments (active or placebo) to a target dose of 3 capsules evening dose in schedule A and B, and 2 capsules morning dose in schedule B. Each dose escalation may be performed after adequate tolerability has been assessed by caregiver and investigator. For example, treatment initiation at Day 1 with 1 capsule (active (Act) or placebo (Plc)) in the evening. Then target up-titration may begin at Day 3 (window+2 days): If no adverse event (AE) related to the study drug is observed by caregiver and/or the investigator, another capsule (active or placebo) is added in the evening. Again at Day 7 (window+2 days), Day 10 (window+2 days and Day 14 (window+2 days) if no AE related to the study drug is observed by caregiver and/or the investigator, another capsule (active or placebo) may be added in the morning. Table V below provides a graphic illustration of the titration schedule.

TABLE V

Titration Schedule

| | | Time | | | | |
|---|---|---|---|---|---|---|
| Schedule | | Days 1 to 2 | Days 3 to 6 | Days 7 to 9 | Days 10 to 13 | Day 14* |
| Schedule A | Evening | 5 mg 1 Capsule | 10 mg 2 Capsules | 15 mg 3 Capsules | 15 mg 3 Capsules | 15 mg 3 Capsules |
| | Morning | None | None | None | Placebo 1 Capsule | Placebo 2 Capsules |
| Schedule B | Evening | 5 mg 1 Capsule | 10 mg 2 Capsules | 15 mg 3 Capsules | 15 mg 3 Capsules | 15 mg 3 Capsules |
| | Morning | None | None | None | 5 mg 1 Capsule | 10 mg 2 Capsules |
| Schedule C | Evening | Placebo 1 Capsule | Placebo 2 Capsules | Placebo 3 Capsules | Placebo 3 Capsules | Placebo 3 Capsules |
| | Morning | None | None | None | Placebo 1 Capsule | Placebo 2 Capsules |

*To end of study treatment period

Evaluation of sleep may include analysis by actigraphy to measure: (1) Sleep Onset Latency (SOL); (2) Total Sleep Time (TST); (3) Wake After Sleep Onset (WASO)=total # of wake epochs after sleep onset; (4) Nocturnal Awakenings (NA); and/or (5) Sleep Efficiency=total sleep time (TST) of time in bed (TIB). Additional evaluation of sleep may include analysis of parent/caregiver logs of sleep patterns that may include: (1) bed time; (2) time of sleep onset; (3) number and duration of awakenings; (4) number of disruptive behavior; (5) time of last awakening; and (6) daytime sleepiness.

Slowed up-titration or delayed up-titration will be acceptable if tolerability does not allow immediate further dose-escalation at any of the above detailed days (3, 7, 10, 14). Down-titration in the case tolerability is not acceptable (e.g., somnolence, dizziness, change in behavior) after a previous up-titration step or during the course of the 12 week treatment, dose can be reduced to the previous level or even further. However, once a tolerable dose has been reached, it shall remain constant for the duration of the treatment period. Once a target dose is achieved the treatment may continue. For example, at Day 14: Earliest day the target dose can be reached (2 capsules in the morning and 3 in the evening) the subject may be kept stable until End of Treatment visit (week 12) unless intolerability requires downtitration.

All subjects will be screened for participation in the study up to 28 days prior to the first dose administration. Inclusion criteria may include one or more of the following: (1) Age≥18 years, ≤40 years; (2) Must possess a clinical diagnosis of AS according to the 2005 consensus criteria with developmental delay, movement or balance disorder, and speech disorder; (3) Must possess a previous or current molecular confirmation of AS; (4) Subjects must be receiving a stable dose of concomitant medications, including anti-epileptic medication, supplements, and special diets, for at least 4 weeks prior to Baseline, and be able to maintain these throughout the duration of the study.

Exclusion Criteria may include one or more of the following: (1) Non-ambulatory subjects (e.g. requiring a wheelchair) not able to perform the tests for Assessment of Motor Ability/Function (as described above); (2) Poorly controlled seizures defined as >3 absence-type seizure per week and/or >1 major seizure episodes per month; (3) Concomitant cardiovascular, respiratory diseases; Concomitant liver disease with alanine aminotransferase or aspartate aminotransferase >2.5×upper limit of normal (ULN); (4) Concomitant renal disease with creatinine above ULN (5) Concomitant hematologic disease with absolute neutrophil count >2×$10^9$/L or platelets <50×$10^9$/L or hemoglobin <80 g/L; (6) Other genetic disorders; (7) Concomitant use of minocycline, levodopa, sleep medication and any other use of any investigational agent, device, and/or investigational procedure 4 weeks prior to Baseline and during the study; (8) At risk of suicide based on ABC-Irritability Subscale Descriptive statistics may be used to summarize all primary and secondary endpoints as well as baseline variables, by treatment group. For continuous variables, n, number of missing values, mean, standard deviation, median, minimum, and maximum will be provided. For categorical variables, frequency and percentage will be presented for each category. Confidence intervals (CI) will be provided where meaningful. All CIs will be two-sided 95% confidence intervals.

Example 8

Prospective Assessment of the Efficacy of Gaboxadol in Patients With Angelman Syndrome This study is designed to determine whether lower doses of gaboxadol lead to an improvement in patients. For example, adolescent patients (age 12-18 years) may have the similar clinical presentation and baseline disease characteristics as the adult population but the reduction in ambulation may be less severe. In these patients it is anticipated that the target benefit of gaboxadol will also include the reduction in ataxia and the improvement in ambulatory function.

In pediatric patients (6 months to 12 years) the diagnosis of Angelman Syndrome is usually made around 1 year of age based on important delay in the development status and eventually persistent seizures. As the child grows older, additional neurologic deficit will contribute to the disease presentation leading to ataxia and walking disability. For these prospective participants, the inclusion criteria for randomization and assessment procedures is similar to that previously described.

After randomization the participants are placed into 6 separate treatment groups (A-F) and a placebo group. Treatment group A receives 7.5 mg gaboxadol in the evening. Treatment group B receives 5 mg gaboxadol in the evening. Treatment group C receives 5 mg gaboxadol in the evening and 2.5 mg gaboxadol in the morning. Treatment group D receives 2.5 mg gaboxadol in the evening. Treatment group E receives 2.5 mg gaboxadol in the evening and 1 mg gaboxadol in the morning. Treatment group F receives 1 mg gaboxadol in the evening.

Example 9

Prospective Assessment of the Efficacy of Gaboxadol in Patients With Fragile X Syndrome This study is designed to determine whether gaboxadol leads to an improvement in one or more symptoms of Fragile X syndrome. Participants are randomized into 6 separate treatment groups (A-F). Inclusion criteria for randomization require patients that have been diagnosed with Fragile X syndrome. For example, patients who are at least moderately ill based on a Clinical Global Impression Severity score of at least 4 and have qualifying scores on the ABC-C and IQ test.

After randomization the participants are separated into 6 treatment groups (A-F) and a placebo group. Treatment group A receives 20 mg gaboxadol in the evening. Treatment group B receives 15 mg gaboxadol in the evening. Treatment group C receives 15 mg gaboxadol in the evening and 5 mg gaboxadol in the morning. Treatment group D receives 10 mg gaboxadol in the evening. Treatment group E receives 10 mg gaboxadol in the evening and 10 mg gaboxadol in the morning. Treatment group F receives 10 mg gaboxadol in the evening and 5 mg gaboxadol in the morning.

Participants are assessed throughout the treatment period to determine whether administration of gaboxadol leads to an improvement in one or more symptoms of Fragile X syndrome. In particular, patients are assessed using one or more primary and secondary outcome measures. Primary Outcome Measures may include:

Change From Baseline in Behavioral Symptoms of Fragile X Syndrome Using the Aberrant Behavior Checklist-Community Edition (ABC-CFX) Total Score;

Global Improvement of Symptoms in Fragile X Using the Clinical Global Impression-Improvement (CGI-I) Scale;

Change From Baseline in Irritability, Lethargy/Withdrawal, Stereotypic Behavior, Hyperactivity, Inappropriate Speech and Social Avoidance Assessed by the Individual Subscales of the ABC-CFX Scale;

Change From Baseline in Repetitive Behaviors Assessed Using the Repetitive Behavior Scale—Revised (RBS-R) Scores;

Visual Analogue Scale (Behavior); Expressive Vocabulary Test; Vineland Adaptive Behavior Scale-II (VABS-II) Adaptive Behavior Composite Score; and Aberrant Behavior Checklist-Community Edition (ABC-C) Composite Score.

Example 10

Prospective Assessment of the Efficacy of Gaboxadol From Baseline to Week 6 and Week 12 in Adolescent and Adult Male Subjects With Fragile X Syndrome The purpose of this study is to investigate the efficacy of treatment with oral administration of gaboxadol capsules in three treatment arms: as 5 mg in the morning daily (QD), 5 mg twice daily (BID) (10 mg/day) and 5 mg three times daily (TID) (15 mg/day) in adolescent and adult males with Fragile X syndrome age 13-22 years. It will be a 12-week randomized, double-blind, parallel group study.

Approximately 30 male subjects aged 13-22 years with Fragile X syndrome, i.e., adults (18-22 years) and adolescents (13-17 years), about 50% of subjects being in each of the two age-groups, will be randomized to the three gaboxadol total daily dose arms in 1:1:1 ratio (n=10/group). The investigator and parent/caretaker will be blinded to the randomization arm.

The capsules will contain 5.645 mg gaboxadol monohydrate, corresponding to 5.0 mg of gaboxadol.

Inclusion criteria:
1. Males age≥13 years, ≤22 years at the time of informed consent
2. Diagnosis of Fragile-X syndrome with a confirmed FMR1 full mutation (≥200 CGG repeats). The diagnosis will be confirmed by genetic testing prior to the subject randomization.
3. Subjects with Clinical Global Impression-Severity (CGI-S) score of 4 (moderately ill) or greater at Screening
4. Receiving a stable dose of concomitant medications, including anti-epileptic and/or behavioral medications, supplements, and special diets, for at least 4 weeks prior to Baseline (prior to randomization).

Screening will be completed up to 21 days before dosing on Day 1. All subjects will receive gaboxadol or placebo in the morning, afternoon and evening during the entire duration of treatment. The 3 dosing schedules of gaboxadol that will be assessed are set forth in Table VI. All subjects will receive treatment for a maximum of 12 weeks.

TABLE VI

Gaboxadol Treatment Groups and Regimen

| Treatment Group | Morning Dose | Afternoon Dose | Evening Dose |
| --- | --- | --- | --- |
| 5 mg QD (5 mg/day) | 5 mg capsule | Placebo capsule | Placebo capsule |
| 5 mg BID (10 mg/day) | 5 mg capsule | Placebo capsule | 5 mg capsule |
| 5 mg TID (15 mg/day) | 5 mg capsule | 5 mg capsule | 5 mg capsule |

Pharmacokinetics-Pharmacodynamics:

Blood samples will be collected for the determination of plasma gaboxadol concentrations at Weeks 0 (Baseline), 2, 6 and 12 at the following timepoints:

One PK sample collected anytime between 0.5 hour and 0.75 hour post-dose

One PK sample collected anytime between 3 hours and 4 hours post-dose

To examine reporter reliability, standardized reliability scores (i.e. inconsistency index) from two of the behavior questionnaires (Conner's and BASC-PRQ) will be collected. BASC-3 PRQ: Description and Consistency Indices: The BASC-3 Parenting Relationship Questionnaire (BASC-3 PRQ) provides information on the relationship between a parent/caregiver and a child across multiple dimensions. It yields the following subscale scores: attachment, communication, discipline practices, involvement, parent confidence, satisfaction with school and relation frustration. BASC-3 Parent Relationship Questionnaire: screening, (week 6), week 12.

A. Sleep Outcome Measures:
1. Children's Sleep Habits Questionnaire (CSHQ). The CSHQ is a parent-reported measure designed to assess sleep behaviors in children and adolescents.
2. Sleep diary—The sleep diary will be completed 7 days prior to the Study Visit (1-week prior to Baseline Visit, Week 1, Week 5, and Week 11, 1 week prior to Follow-up visit) only. It should be completed for 7 consecutive days.
3. Clinician questionnaire
    a. Pediatric Sleep CGI in Autism Rater form: A recently developed tool specifically for the autism population used in a clinical trial and validated with the CSHQ, actigraphy and clinical interview.
4. Participant completed measure. The subjects will be provided with a wearable wrist-watch-like device, ActiWatch (commercially available from Phillips North America LCC 3000 Minuteman Road, Andover, Mass. 01810). The ActiWatch is an actigraphy device allows for the recording of wrist movements. It is used to analyze circadian rhythms, sleep-wake patterns, and activity. The ActiWatch will be worn 7 days prior to the Study Visit (1-week prior to Baseline Visit, Week 1, Week 5, and Week 11, 1 week prior to Follow-up visit) only. It should be worn continuously throughout the day and night for 7 consecutive days. These data will be correlated with the sleep diary.

B. Behavioral Outcome Measures:

Parent/Caretaker Completed Measures
1. Aberrant Behavior Checklist—Community (ABC-C). The ABC-C is a parent-completed measure that assesses a wide range of behaviors, including irritability, lethargy/social withdrawal, inappropriate speech, hyperactivity, and stereotypic behavior, and social avoidance.
2. Anxiety, Depression, and Mood Scales (ADAMS). The ADAMS is a parent/caregiver-completed measure about their observations of the subject's psychosocial well-being and consists of 28 items, grouped into 5 subscales that assess the frequency and severity of manic/hyperactive behavior, depressed mood, social avoidance, general anxiety, obsessive behavior.
3. Repetitive Behavior Scale-Revised (RBS-R). The RBS-R is a parent-rated assessment of repetitive behavior with six behavior subscales: stereotyped, ritualistic, self-injurious, compulsive, restricted, and sameness.
4. Conner's Questionnaire. The Conner's $3^{rd}$ Edition Parent Short Form is an assessment tool used to obtain the parent's/caregiver's observations about the participant's behavior through 45 items. This instrument is designed to assess Attention Deficit/Hyperactivity Disorder (ADHD). Conner's Long Form (needed for inconsistency index): Screening and Conner's Short Form: Week 6 and Week 12.
5. Short Sensory Profile-2 is a caregiver's questionnaire to evaluate a child's sensory processing patterns in the context of home, school, and community-based activities.

C. Global and Functional Outcome Measures:

Parent Questionnaire

Parent Global Impression Scale (PGI-S). Parents or caregivers will complete this assessment to evaluate the severity of their child's symptoms.

Clinician/Rater Completed Measures
1. Top 3 Concerns Visual Analog Scale (VAS). The Clinician will also assess key areas of concerns/impairments identified by the caregivers in the domains of Behavior, Sleep, Language, Motor, Cognition, Social, and Self-Care skills.
2. Vineland Adaptive Behavior Scale-3$^{rd}$ Edition Caregiver Interview Form (VABS-3). The Vineland-3 will be used to evaluate communication, socialization, and daily living skills of subjects to assess their overall adaptive functioning.
3. Clinical Global Impressions (Severity [CGI-S] and Improvement [CGI-I] scales). CGI-S will be used by the investigator to assess severity of symptoms, while the CGI-I will be used to assess improvement from baseline. The CGI-S has been adapted to capture specific characteristics commonly present in the FXS population.
4. PedsQL Family Impact Module version 2 is a parent completed questionnaire developed to measure the impact of a parent caring for a subject with an acute or chronic condition. It consists of six scales covering 1) physical functioning, 2) emotional functioning, 3) social functioning, 4) cognitive functioning, 5) communication, 6) worry, 7) daily activities, 8) family relationships.

D. Cognitive/Automated Outcome Measure
Participant Completed Measure
1. Computerized measurement of cognition using the Test of Attentional Performance for Children (KiTAP). The KiTAP is an automated computer-based assessment of attentional performance developed and normed for a pediatric population. The task displays an "enchanted castle" animation and investigates performance on 8 sub scales—alertness, distractibility, divided attention, flexibility, Go/No Go, sustained attention, vigilance, visual scanning. The assessment of interest for this study will include alertness, distractibility, flexibility, and Go/No Go subtests.
2. Evoked Resting Potential (ERP)-: EEG will be utilized to characterize ERP in individuals with Fragile X syndrome and to assess treatment response and associated changes in the cortical activity. Participants will passively listen to 150 pairs (S1, S2) of 5 msec broadband noise bursts (75 dB) separated by an inter-stimulus interval of 500 msec. Inter-trial intervals will be 4,000 msec (on average), for a total task duration of 11.25 minutes. Data from an EEG will be acquired continuously at a 1000 Hz sampling rate, and will be filtered online at 0.1-100 Hz, amplified (12,500×), and digitized (1000 Hz). Participants will view a standard silent movie of their choice during EEG recording.
   a. Repeatable Battery for the Assessment of Neuropsychological Status (RBANS) is to identify and characterize cognitive decline in older adult and as a neuropsychological battery for younger patients). It is an individually administered test that can be used to measure cognitive improvement or decline. The full battery consists of 12 subtests to assess immediate memory, visuospatial abilities, language, attention, and delayed memory. In this study, 6 subtests of the RBANS will be used: list learning (immediate memory), list recall (delayed memory), list recognition (delayed memory index), story memory (immediate memory index), story recall (Delayed Memory Index), picture naming (language index).

Efficacy endpoints derived from the COAs as listed above will be analyzed for the Full Analysis Set (all subjects that received at least one dose of study drug and had at least one efficacy evaluation) in an exploratory fashion. Descriptive statistics, 95% CIs and/or box-whisker plots will be displayed for baseline, interim visit, final visit and changes from baseline to both scheduled post-baseline visits for all randomized arms combined. For selected efficacy endpoints, the same analyses will be repeated for the three total daily dose arms. The correlation of CSHQ-T/DS (children's sleep habits Questionnaire) against the corresponding ActiWatch data will be assessed by correlation coefficients (Pearson Product Moment Correlation coefficients or Spearman Correlation coefficients, as appropriate) and the corresponding scatter plots.

Example 11

Prospective Assessment of the Efficacy of Gaboxadol in Patients With Fragile X Syndrome This study is designed to determine whether lower doses of gaboxadol will lead to an improvement in younger patients or patients with less severe clinically evaluated symptoms. For these participants, the inclusion criteria for randomization and assessment procedures will be similar to that previously described.

After randomization the participants are randomized into 6 separate treatment groups (A-F) and a placebo group. Treatment group A receives 7.5 mg gaboxadol in the evening. Treatment group B receives 5 mg gaboxadol in the evening. Treatment group C receives 5 mg gaboxadol in the evening and 2.5 mg gaboxadol in the morning. Treatment group D receives 2.5 mg gaboxadol in the evening. Treatment group E will receive 2.5 mg gaboxadol in the evening and 1 mg gaboxadol in the morning. Treatment group F receives 1 mg gaboxadol in the evening.

Example 12

Prospective Assessment of the Efficacy of Gaboxadol in Patients With Fragile X-Associated Tremor/Ataxia Syndrome This protocol is directed to treating symptomatic permutation carriers who have pre-FXTAS or FXTAS symptoms including neuropathy, central pain symptoms, insomnia, and full FXTAS involving tremor and ataxia which is often associated with cognitive decline.

This will be a two-site study. Participants will be individuals with the premutation and FXTAS. FMR1 CGG repeat lengths will be quantified in all subjects using conventional procedures. FXTAS will be diagnosed following published criteria (Bacalman et al., *Clin Psychiatry* 2006, 67:87-94; Jacquemont et al., *Lancet Neurol* 2003, 6:45-55). The study will involve a controlled trial of gaboxadol lasting three months followed by a three month open-label so that those individuals that were treated for the first three months on gaboxadol would continue for a second three months and those individuals on placebo would go on gaboxadol for the second three months. Each site would enroll 20 patients per year for a total of 40 at each site over a two year period and between the sites there would be 80 patients participating.

Identical appearing tablets containing either gaboxadol or placebo will be administered. After randomization the participants are randomized into separate treatment groups and a placebo group. Treatment group A receives 7.5 mg gaboxadol in the evening. Treatment group B receives 5 mg gaboxadol in the evening. Treatment group C receives 5 mg gaboxadol in the evening and 2.5 mg gaboxadol in the morning. Treatment group D receives 2.5 mg gaboxadol in the evening. Treatment group E receives 2.5 mg gaboxadol in the evening and 1 mg gaboxadol in the morning. Treatment group F receives 1 mg gaboxadol in the evening.

At baseline, and then at three months, and then at six months, the following studies would be done: An assessment of the severity of pain using a pain index and documentation of the type of pain; and a sleep diary will be implemented. Quantitative measures will be implemented using an actometer to observe the severity of sleep disturbances over a one week period of time. Neuropsychological measures would include the Mini-Mental State Examination (MMSE), Behavioral Dyscontrol Scale (BDS-II), Wechsler Memory Scale IV, the California Verbal Learning Test 2 (CVLT-2), Repeatable Battery for the Assessment of Neuropsychological Status (RBANS) and the SCL-90 for a determination of emotional improvements. Any improvements in the MMSE, the BDS-II, and in event related potential (ERP) studies, particularly with the N4 Repetition Paradigm, and in volumetric changes in the hippocampus will be assessed. Motor assessments will be made which documents abnormalities in those with FXTAS compared to other movement disorders. An FXTAS rating scale will be utilized. MRI volumetric studies with the 3Tesla MRI along with DTIs will be conducted. Eye-tracking measures looking at an inhibitory paradigm will be evaluated. The P6 repetition effect over a six month will be evaluated. All of these measures will be at baseline, three months, and six months. Baseline cognitive testing using the Wechsler Scale and WAIS-IV will be carried out also. This could be repeated after one year but typically not sooner. Improvement in neuropathy may be detected and followed through clinical examination using neurodiagnostic studies or electrophysiological studies.

Example 13

Prospective Assessment of the Efficacy of Gaboxadol in Patients With Fragile X-Associated Tremor/Ataxia Syndrome This study is designed to determine whether gaboxadol leads to an improvement in cognitive symptoms, i.e., attentional processes which are fundamental to executive function/dysfunction associated with Fragile X-associated tremor/ataxia syndrome (FXTAS) and involves a placebo-controlled, double-blind, randomized clinical trial and an auditory "oddball" task. Participants will be individuals with FXTAS. FMR1 CGG repeat lengths will be quantified in all subjects using conventional procedures. FXTAS will be diagnosed following published criteria (Bacalman et al., Clin Psychiatry 2006, 67:87-94; Jacquemont et al., Lancet Neurol 2003, 6:45-55). For the main gaboxadol trial, 200 potential participants will be screened for eligibility. Randomization to either placebo or gaboxadol will be blinded to all study personnel, investigators, and participants until the end of the one year trial period. Participants will participate in an auditory "oddball"/event related potentials (ERPs) experiment.

Identical appearing tablets containing either gaboxadol or placebo will be administered. After randomization the participants are randomized into 6 separate treatment groups (A-F) and a placebo group. Treatment group A receives 7.5 mg gaboxadol in the evening. Treatment group B receives 5 mg gaboxadol in the evening. Treatment group C receives 5 mg gaboxadol in the evening and 2.5 mg gaboxadol in the morning. Treatment group D receives 2.5 mg gaboxadol in the evening. Treatment group E receives 2.5 mg gaboxadol in the evening and 1 mg gaboxadol in the morning. Treatment group F receives 1 mg gaboxadol in the evening.

In the auditory "oddball" experiment, patients will be instructed to detect an infrequent "oddball" tone embedded in a train of non-target standard tones. Subjects will press a button to each target detected and also keep a mental count of the number of targets in that experimental block. Prior studies in premutation carriers using the same "oddball" paradigm have demonstrated an altered frontal P300 (P3) ERP component in FXTAS patients, which tracks their executive dysfunction. See, Yang et al., Ann Neurol 74, 275-283 (2013); Yang et al., Cereb Cortex 23, 2657-2666 (2013). In these studies and others, the earlier abnormalities of prolonged N100 latency and reduced P200 (P2) amplitude were also found in a predominately male FXTAS group but not in female premutation carriers asymptomatic of FXTAS9.

Neuropsychological testing will involve examining each patient's EEG. Accordingly, EEG during a two-stimulus auditory oddball experiment will be recorded in a sound-attenuated, dimly-lit chamber. Lower (113 Hz) and higher (200 Hz) frequency pure tones will be presented at 40 dB above individual hearing level in 4 blocks, each containing 100 tones, with a stimulus onset asynchrony jittered from 1.0-1.5 seconds. Prior to each block, subjects will be instructed to respond to the infrequent (probability equaling 25%) "oddball" tones (high or low target tones, counterbalanced across blocks). A dual task will be employed in which subjects are instructed to press a button to each target tone, and to also keep a mental count of the number of targets in each block. The mental count of target tones will be reported immediately following completion after each block. 32-channel EEG will be recorded with a Nicolet-SM-2000 amplifier (band-pass=0.016-100 Hz, sampled at 250 Hz). Data Analysis will involve the |count-hit| discrepancy in each block (i.e., the absolute value of the difference between correct button-presses and mental count to target tones within a block) will be calculated for each participant, as an inverse measure (i.e., a lower value represents better performance) of attention/working memory performance during the oddball task. Event-locked EEG segments contaminated with blinks, eye movements, excessive muscle activity, or amplifier blocking will be rejected using a semi-automated computer algorithm. Artifact-free EEG segments of 1024 ms (with a 100 ms pre-stimulus baseline period, and 924 ms post-stimulus onset) will be averaged by experimental condition to obtain the ERPs. Mean amplitude and local peak latency of 4 ERP components will be quantified in the following time windows: N100 (N1, 70-150 ms), P2 (160-260 ms), N200 (N2, 170-300 ms), and P3 (300-650 ms). The waveforms to both target and standard tones will be used to measure N1. The P2 will be measured from ERPs to standard tones. The N2 component is defined from the difference wave (ERPs to targets minus standards). The P3 will be measured from both the difference wave and the ERP waveform to targets. ERP measures will be submitted to repeated-measures ANOVAs (SPSS 22, IBM) with the between-subjects factor of treatment, and the within-subjects factors of visit and electrode. Analyses of N1 and P2 will include 4 fronto-central electrodes (Fz, Cz, FC1/2). Five central channels (Cz, FC1/2, CP1/2) will be used for the N2 analyses. P3 analyses will be carried out with 26 scalp electrodes (all except FP1/2). The Greenhouse-Geiser correction will be used to adjust for violations of sphericity, where appropriate. To further characterize the modulatory effects of gaboxadol on the P2 component, a habituation analysis will be conducted for P2 amplitude. P2 mean amplitude in response to the first 30 standard tones will be compared to the amplitude of response to the last 30 standard tones within the first block of each study, with the between-subjects factor of treatment, and the within-subjects factors of visit, trial position, and electrode. Data from a group of 16 age-matched normal controls, each of whom will have only underwent one ERP recording, will be used to demonstrate the normal habituation effect. Linear regression will be used to examine the correlations between changes (1-year follow-up minus baseline) in the |count-hit| discrepancy and in ERP measures for which significant treatment effects are shown. Correlations between local peak amplitudes of P2 (measured after application of a 30 Hz low-pass filter) and CGG repeats will be tested.

Those skilled in the art will recognize, or be able to ascertain using no more than routine experimentation, many equivalents to the specific embodiments described herein. Such equivalents are intended to be encompassed by the claims.

What is claimed is:

1. A method of treating Prader-Willi syndrome consisting essentially of administering to a patient in need thereof gaboxadol or a pharmaceutically acceptable salt thereof.

2. The method of claim 1, wherein the patient is administered about 1 mg to about 30 mg gaboxadol or a pharmaceutically acceptable salt thereof.

3. The method of claim 1, wherein the patient is administered about 1 mg to about 25 mg gaboxadol or a pharmaceutically acceptable salt thereof.

4. The method of claim 1, wherein the patient is administered about 1 mg to about 15 mg gaboxadol or a pharmaceutically acceptable salt thereof.

5. The method of claim 1, wherein the patient is administered about 1 mg to about 10 mg gaboxadol or a pharmaceutically acceptable salt thereof.

6. The method of claim 1, wherein the in vivo plasma profile of the patient 6 hours after administration of the gaboxadol or pharmaceutically acceptable salt thereof is reduced by more than 50%.

7. The method of claim 1, wherein the $AUC_{6-12}$ of the patient 6 hours after administration of the gaboxadol or pharmaceutically acceptable salt thereof is less than 75% of the administered dose.

8. The method of claim 1, wherein the method provides improvement in the patient for more than 8 hours.

9. The method of claim 1 wherein the method provides improvement in the patient for at least 12 hours.

10. The method of claim 1 wherein the method provides improvement in the patient for more than 12 hours after administration.

11. A method of treating Prader-Willi syndrome consisting essentially of administering to a patient in need thereof a composition containing gaboxadol or a pharmaceutically acceptable salt thereof and a carrier wherein the method provides an in vivo plasma profile comprising a $C_{max}$ less than about 400 ng/ml.

12. A method of treating Prader-Willi syndrome consisting essentially of administering to a patient in need thereof a composition containing gaboxadol or a pharmaceutically acceptable salt thereof and a carrier wherein the method provides an in vivo plasma profile comprising a $AUC_{6-12}$ of less than about 900 ng•hr/ml.

13. The method of claim 1 wherein the method provides improvement in at least one symptom selected from the group consisting of ataxia, gait, speech impairment, vocalization, cognition, motor activity, hypotonia and obesity.

* * * * *